United States Patent
Stahmann

(10) Patent No.: US 7,798,973 B2
(45) Date of Patent: Sep. 21, 2010

(54) DETECTION OF HYPOVOLEMIA USING IMPLANTABLE MEDICAL DEVICE

(75) Inventor: Jeffrey E. Stahmann, Ramsey, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1191 days.

(21) Appl. No.: 11/249,611

(22) Filed: Oct. 13, 2005

(65) Prior Publication Data

US 2007/0088220 A1    Apr. 19, 2007

(51) Int. Cl.
*A61B 5/02* (2006.01)
(52) U.S. Cl. .................. 600/485; 600/484; 600/483; 600/486
(58) Field of Classification Search ......... 600/483–486; 607/9–17
See application file for complete search history.

(56) References Cited

U.S. PATENT DOCUMENTS

| | | | |
|---|---|---|---|
| 5,261,876 A | 11/1993 | Popovich et al. | |
| 5,368,040 A | 11/1994 | Carney | |
| 5,743,267 A * | 4/1998 | Nikolic et al. | 600/483 |
| 6,298,267 B1 | 10/2001 | Rosborough et al. | |
| 6,299,583 B1 | 10/2001 | Eggers et al. | |
| 6,804,656 B1 | 10/2004 | Rosenfeld et al. | |
| 2002/0198513 A1 * | 12/2002 | Lebel et al. | 604/891.1 |
| 2004/0147969 A1 * | 7/2004 | Mann et al. | 607/17 |
| 2005/0154321 A1 | 7/2005 | Wolinsky et al. | |
| 2005/0288604 A1 * | 12/2005 | Eigler et al. | 600/561 |
| 2006/0009818 A1 | 1/2006 | Von Arx et al. | |
| 2006/0041281 A1 | 2/2006 | Von Arx et al. | |
| 2006/0064133 A1 | 3/2006 | Von Arx et al. | |
| 2006/0064134 A1 | 3/2006 | Mazar et al. | |
| 2006/0064142 A1 | 3/2006 | Chavan et al. | |
| 2006/0064143 A1 | 3/2006 | Von Arx et al. | |
| 2006/0122522 A1 | 6/2006 | Chavan et al. | |

FOREIGN PATENT DOCUMENTS

| | | | |
|---|---|---|---|
| WO | WO-03041587 A3 | 5/2003 | |
| WO | WO-2007047288 A1 | 4/2007 | |

OTHER PUBLICATIONS

"International Search Report and Written Opinion for Application No. PCT/US2006/039671", (Mar. 29, 2007),17 pages.

(Continued)

*Primary Examiner*—Robert L Nasser
*Assistant Examiner*—Michael D'Angelo
(74) *Attorney, Agent, or Firm*—Schwegman, Lundberg & Woessner, P.A.

(57) ABSTRACT

An implantable medical device receives a physiological signal indicative of circulatory blood volume and detects hypovolemia from that physiological signal. In one embodiment, an implantable pulmonary artery pressure (PAP) senses a PAP signal, and the implantable medical device detects hypovolemia from the PAP signal.

37 Claims, 17 Drawing Sheets

OTHER PUBLICATIONS

Adamson, P. B., et al., "Ongoing Right Ventricular Hemodynamics in Heart Failure", *Clinical Value of Measurements Derived from am Implantable Monitoring System*, (Feb. 19, 2003),565-571.

Braunschweig, F., et al., "Continous haemodynamic monitoring during withdrawal of diuretics in patients with congestive heart failure", *Department of Cardiology and Clinical Physiology*, (Jan. 2002),59-69.

Lowe, J., et al., "Adverse reactions to frusemide in hospital inpatients", *British Journal of Medicine*, 2(6186), (Aug. 11, 1979), 360-2.

McGhee, B. H., et al., "Monitoring arterial blood pressure: what you may not know", *Crit Care Nurse*, 22(2), (Apr. 2002), 60-4, 66-70, 73 passim.

Stahmann, Jeffrey E., et al., "Method and Apparatus for Pulmonary Artery Pressure Signal Isolation", U.S. Appl. No. 11/249,624, filed Oct. 13, 2005, 59 Pages.

Stillwell, Susan B., et al., "Pocket guide to cardiovascular care", *St. Louis : Mosby*, 2nd Edition,(1994), 81-83.3.

\* cited by examiner

DETECTION OF HYPOVOLEMIA USING IMPLANTABLE MEDICAL DEVICE

TECHNICAL FIELD

This document relates generally to implantable medical systems and particularly, but not by way of limitation, to an implantable medical device providing for detection of hypovolemia.

BACKGROUND

The heart is the center of a person's circulatory system. The left portions of the heart, including the left atrium (LA) and left ventricle (LV), draw oxygenated blood from the lungs and pump it to the organs of the body to provide the organs with their metabolic needs for oxygen. The right portions of the heart, including the right atrium (RA) and right ventricle (RV), draw deoxygenated blood from the body organs and pump it to the lungs where the blood gets oxygenated. Heart failure occurs when the heart fails to pump sufficient blood to supply the organs with their metabolic needs for oxygen. The insufficiency of blood supply to the kidneys may impair renal function to the extent causing excessive fluid retention in the body, known as decompensation.

Drugs such as diuretics are used to treat decompensation. Diuretics increases removal of liquid from the body by increasing urinary flow. A known side effect associated with excessive dose of diuretics is hypovolemia, or decreased circulatory blood volume. Other causes of hypovolemia include dehydration and bleeding. The symptoms of hypovolemia include dizziness, nausea, and extreme thirst. Hypovolemia may develop into a hypovolemic shock, in which the heart is unable to supply enough blood to the body due to the low circulatory blood volume, causing organs of the body to fail.

To manage a treatment of decompensation for heart failure patients, such as a drug therapy using diuretics, there is a need to monitor for hypovolemia.

SUMMARY

An implantable medical device receives a physiological signal indicative of circulatory blood volume and detects hypovolemia from that physiological signal. In one embodiment, an implantable pulmonary artery pressure (PAP) senses a PAP signal, and the implantable medical device detects hypovolemia from the PAP signal.

In one embodiment, a system for detecting hypovolemia includes a physiological sensor and an implantable medical device. The physiological sensor senses a physiological signal indicative of circulating blood volume. The implantable medical device receives the physiological signal from the physiological sensor and includes a signal processor and a hypovolemia detector. The signal processor processes the physiological signal. The hypovolemia detector detects a hypovolemia using the processed physiological signal and produces a hypovolemia detection signal indicative of the detection of hypovolemia.

In one embodiment, a method for operating an implantable medical device to detect hypovolemia is provided. A physiological signal indicative of a volume of circulating blood is received. Hypovolemia is detected from the physiological signal using the implantable medical device.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

The drawings, which are not necessarily drawn to scale, illustrate generally, by way of example, but not by way of limitation, various embodiments discussed in the present document.

DETAILED DESCRIPTION

Figure 1:
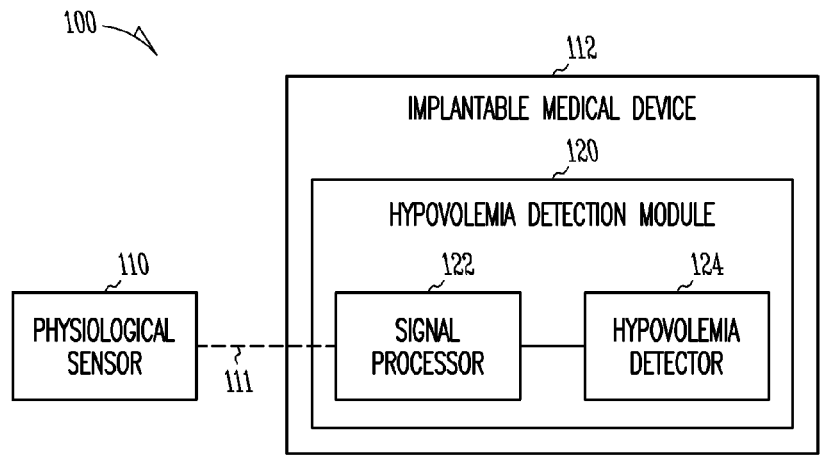
FIG. 1 is a block diagram illustrating an embodiment of a medical system for detecting hypovolemia using an implantable medical device.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description provides examples, and the scope of the present invention is defined by the appended claims and their legal equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this documents and those documents so incorporated by reference, the usage in the incorporated reference(s) should be considered supplementary to that of this document; for irreconcilable inconsistencies, the usage in this document controls.

In this document, "mean" (such as in "mean PAP", i.e., MPAP) includes mean and other notations of central tendency, such as average, mode, and median.

This document discusses a medical system including an implantable medical device that detects hypovolemia. Examples of known signs of hypovolemia include decreased PAP, weight loss, increased heart rate, increased respiratory rate, decreased central venous pressure (CVP), postural hypotension, decreased pulse pressure, delayed dicrotic notch in arterial pressure, decreased urine output, increased hemoglobin, increased hematocrit, and increased BUN-to-creatine ratio. The medical system includes a physiological sensor and an implantable medical device. The physiological sensor senses one or more physiological signals indicative of the circulatory blood volume in a patient. The implantable medical device detects hypovolemia when the one or more physiological signals indicate an abnormally low circulatory blood volume. The physiological sensor includes one or more of a blood pressure sensor, an electrocardiogram sensor, a respiratory sensor, a blood impedance sensor, a cardiac output sensor, a creatinine sensor, a blood urea nitrogen sensor, a hemoglobin sensor, a hematocrit sensor, and a body weight sensor.

In one embodiment, the physiological sensor includes an implantable PAP sensor that senses a PAP signal. A PAP attribute is detected from the sensed PAP signal. Hypovolemia is detected when the PAP attribute is out of its predetermined normal range. In a specific embodiment, the PAP attribute is a mean PAP (MPAP). The MPAP is detected from the sensed PAP signal and compared to a predetermined threshold. A detection of hypovolemia is declared when the MPAP drops below the predetermined threshold. In a further embodiment, one or more additional sensors are used to sense one or more additional signals indicative of hypovolemia to enhance the detection. The use of the implantable PAP sensor and the implantable medical device allows detection of hypovolemia using an implantable system. In one embodiment, the implantable medical device communicates the detection of hypovolemia to a device at a remote location via telemetry, thereby allowing continuous monitoring of the patient by a physician or other caregiver. In another embodiment, the implantable medical device communicates the detection of hypovolemia to an external system for management of a therapy, such as a drug therapy using diuretics. In another embodiment, the implantable medical device delivers a therapy and adjusts that therapy in response to the detection of hypovolemia.

FIG. 1 is a block diagram illustrating an embodiment of a medical system 100 for detecting hypovolemia using a physiological sensor 110 and an implantable medical device 112. Physiological sensor 110 senses a physiological signal indicative of a volume of circulating blood. The physiological signal is transmitted to implantable medical device 112 through a communication link 111. Implantable medical device 112 includes a hypovolemia detection module 120, which includes a signal processor 122 and a hypovolemia detector 124. Signal processor 122 processes the physiological signal. Hypovolemia detector 124 detects hypovolemia using the processed physiological signal and produces a hypovolemia detection signal indicative of the detection of hypovolemia.

While a system including an implantable PAP sensor communicatively coupled to an implantable medical device is specifically discussed below as an illustrative example, the present subject matter is not limited to embodiments using an implantable system. For example, physiological sensor 110 can be implantable or non-implantable and can include any one or more sensors that sense one or more physiological signals indicative of the circulatory blood volume of a person, and hypovolemia detection module 120 can be implemented in a non-implantable device. In various embodiments, hypovolemia detection module 120, including its specific embodiments as discussed below, is implemented by hardware, software, or a combination of hardware and software. In various embodiments, hypovolemia detection module 120 includes elements such as those referred to as modules below that are each an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 2:
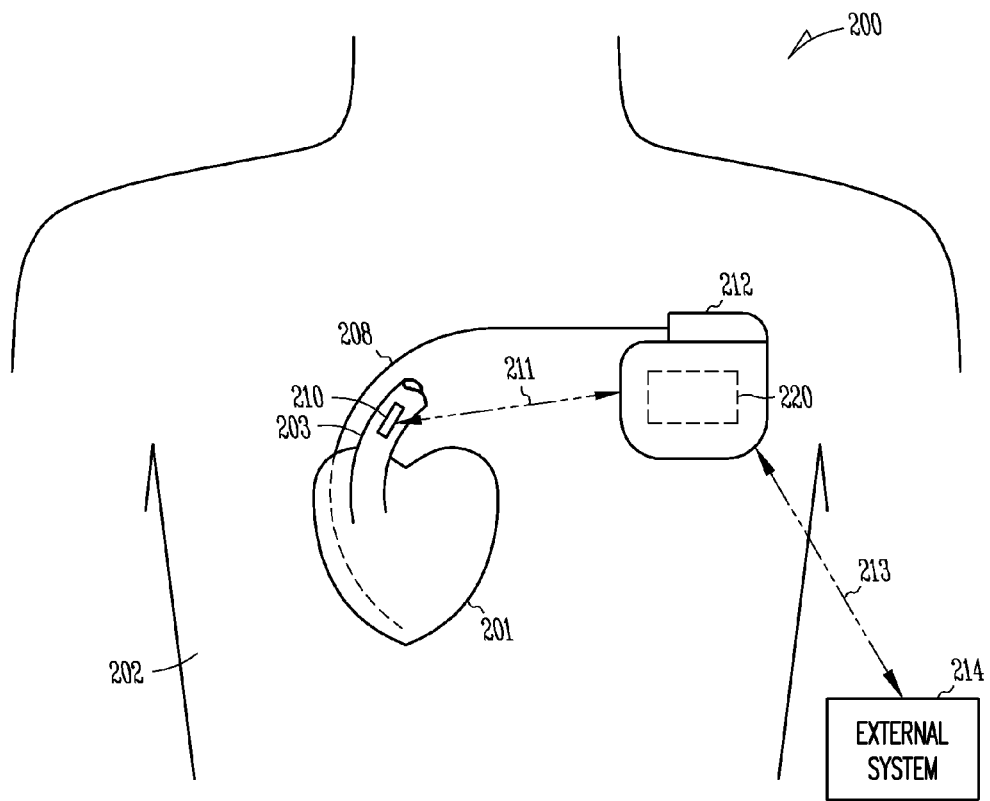
FIG. 2 is an illustration of a specific embodiment of the medical system and portions of an environment in which the medical system operates.

FIG. 2 is an illustration of an embodiment of a medical system 200 and portions of an environment in which system 200 operates. System 200 includes an implantable PAP sensor 210, an implantable medical device 212, an external system 214, a communication link 211 between implantable PAP sensor 210 and implantable medical device 212, and a communication link 213 between implantable medical device 212 and external system 214.

Implantable PAP sensor 210 is a specific embodiment of physiological sensor 110 and senses a PAP signal. As illustrated in FIG. 2, implantable PAP sensor 210 and implantable medical device 212 are implanted in a patient's body 202 that has a pulmonary artery 203 connected to a heart 201. The right ventricle of heart 201 pumps blood through pulmonary artery 203 to the lungs of body 202 to get oxygenated. Implantable PAP sensor 210 is a pressure sensor configured for being mounted on a portion of the interior wall of pulmonary artery 203 to sense the PAP signal. The sensed PAP signal is transmitted to implantable medical device 212 through communication link 211. In one embodiment, communication link 211 is a wired communication link formed by a lead connected between implantable PAP sensor 210 and implantable medical device 212. In another embodiment, communication link 211 is an intra-body wireless telemetry link. Implantable medical device 212 is a specific embodiment of implantable medical device 112 and includes a hypovolemia detection module 220. Hypovolemia detection module 220 is a specific embodiment of hypovolemia detection module 120 and detects hypovolemia using the PAP signal sensed by implantable PAP sensor 210. In various embodiments, implantable medical device 212 includes one or more of a physiological monitor, a pacemaker, a cardioverter/defibrillator, a cardiac resynchronization therapy (CRT) device, a cardiac remodeling control therapy (RCT) device, a neural stimulator, a drug delivery device or a drug delivery controller, and a biological therapy device. In various embodiments in which one or more signals in addition to the PAP signal are sensed, and/or one or more therapies are delivered, a lead system 208 provides for electrical and/or other connections between body 202 and implantable medical device 212. In various embodiments, lead system 208 includes leads for sensing physiological signals and delivering pacing pulses, cardioversion/defibrillation shocks, neural stimulation pulses, pharmaceutical agents, biological agents, and/or other types of energy or substance for treating cardiac disorders. In one embodiment, as illustrated in FIG. 2, lead system 208 provides for such electrical and/or other connections between heart 201 and implantable medical device 212.

External system 214 allows a user such as a physician or other caregiver to control the operation of implantable medical device 212 and obtain information acquired by implantable medical device 212. In one embodiment, external system 214 includes a programmer communicating with implantable medical device 212 bi-directionally via communication link 213, which is a telemetry link. In another embodiment, external system 214 is a patient management system including an external device communicating with a remote device through a telecommunication network. The external device is within the vicinity of implantable medical device 212 and communicates with implantable medical device 212 bi-directionally via telemetry link 213. The remote device allows the user to monitor and treat the patient from a distant location. The patient monitoring system is further discussed below, with reference to FIG. 7.

Communication link 213 provides for data transmission from implantable medical device 212 to external system 214. This includes, for example, transmitting real-time physiological data acquired by implantable medical device 212, extracting physiological data acquired by and stored in implantable medical device 212, extracting therapy history data stored in implantable medical device 212, and extracting data indicating an operational status of implantable medical device 212 (e.g., battery status and lead impedance). The real-time and stored physiological data acquired by implantable medical device 212 include data related to the detection of hypovolemia, such as data representative of the PAP signal, parameters related to the PAP signal, recorded history of hypovolemia detection, and warning messages related to hypovolemia detection. Telemetry link 213 also provides for data transmission from external system 214 to implantable medical device 212. This includes, for example, programming implantable medical device 212 to acquire physiological data, programming implantable medical device 212 to perform at least one self-diagnostic test (such as for a device operational status), and programming implantable medical device 212 to deliver at least one therapy.

Figure 3:
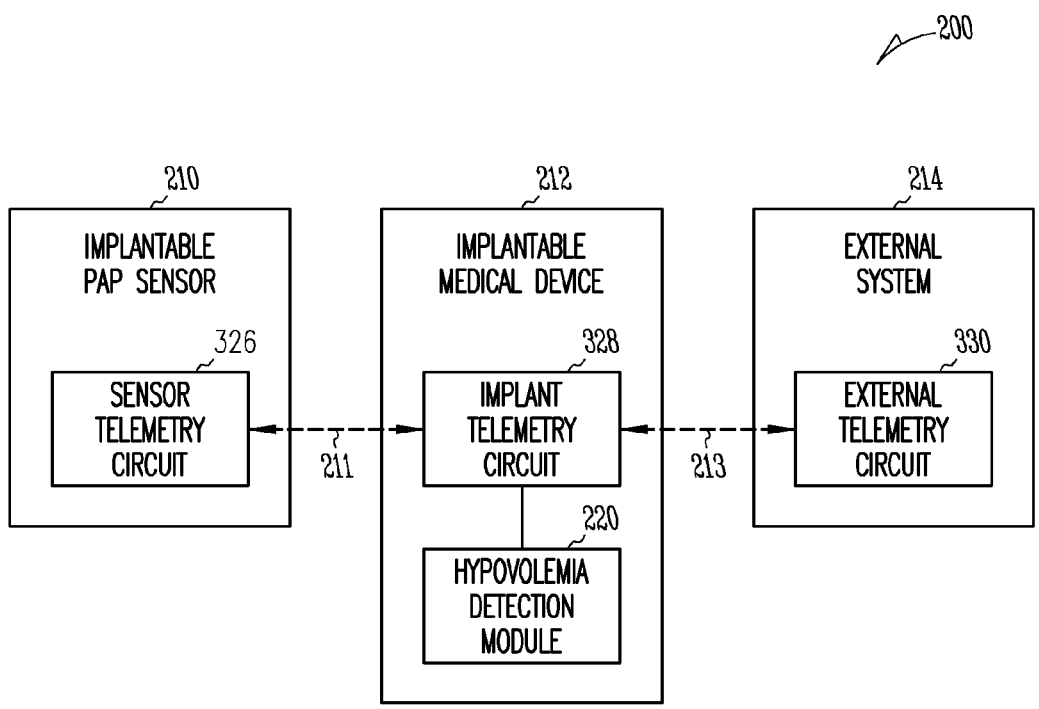
FIG. 3 is a block diagram illustrating an embodiment of portions of a circuit of the medical system of FIG. 2.

FIG. 3 is a block diagram illustrating an embodiment of portions of a circuit of system 200. Implantable PAP sensor 210 includes a sensor telemetry circuit 326 in addition to its pressure-sensing element. Implantable medical device 212 includes an implant telemetry circuit 328, in addition to hypovolemia detection module 220 and, if applicable, other monitoring and/or therapeutic elements. In one embodiment, implant telemetry circuit 328 includes a sub-circuit supporting communication link 211 and another sub-circuit supporting communication link 213. External system 214 includes an external telemetry circuit 330, in addition to programming and other patient management elements.

In one embodiment, communication link 211 is an ultrasonic telemetry link. Sensor telemetry circuit 326 includes an ultrasonic telemetry transmitter that transmits the PAP signal by modulating an ultrasonic signal using the PAP signal and transmitting the modulated ultrasonic signal. Implant telemetry circuit 328 includes an ultrasonic telemetry receiver that receives the PAP signal by demodulating the modulated ultrasonic carrier signal. An example of an intra-body ultrasonic telemetry system is discussed in U.S. patent application Ser. No. 10/888,956, entitled "METHOD AND APPARATUS OF ACOUSTIC COMMUNICATION FOR IMPLANTABLE MEDICAL DEVICE," filed on Jul. 9, 2004, assigned to Cardiac Pacemakers, Inc., which is incorporated herein by reference in its entirety. In another embodiment, communication link 211 is a far-field radio-frequency (RF) telemetry link. Sensor telemetry circuit 326 includes a far-field RF telemetry transmitter that transmits the PAP signal by modulating an electromagnetic signal using the PAP signal and transmitting the modulated electromagnetic signal. Implant telemetry circuit 328 includes a far-field RF telemetry receiver that receives the PAP signal by demodulating the modulated electromagnetic carrier signal. In another embodiment, communication link 211 is an inductive telemetry link. Sensor telemetry circuit 326 includes an inductive telemetry transmitter that transmits the PAP signal by modulating a magnetic field using the PAP signal. Implant telemetry circuit 328 includes an inductive telemetry receiver that receives the PAP signal by demodulating the modulated magnetic field. In one embodiment, communication link 211 is a bidirectional telemetry link that allows for transmission of the PAP signal from implantable PAP sensor 210 to implantable medical device 212 as well as transmission of signals such as command signals from implantable medical device 212 to implantable PAP sensor 210 for controlling the operation of implantable PAP sensor 210. Sensor telemetry circuit 326 and implant telemetry circuit 328 each include an ultrasonic, far-field RF, or inductive telemetry transceiver to support communication link 211.

In various embodiments, communication link 213 is a bidirectional ultrasonic, far-field RF, or inductive telemetry link. Implant telemetry circuit 328 and external telemetry circuit 330 each include an ultrasonic, far-field RF, or inductive telemetry transceiver to support communication link 213.

Communication links 211 and 213 are illustrated in, and discussed with reference to, FIG. 3 for illustrative but not restrictive purposes. Other communicating schemes are useable to transmit the PAP signal and/or other signals from implantable PAP sensor 210 to implantable medical device 212, from implantable medical device 212 to external system 214, or from implantable PAP sensor 210 to external system 214. In one embodiment, an insulated wire can provide an electrical connection between implantable PAP sensor 210 and implantable medical device 212 for transmitting the PAP signal. In another embodiment, implantable PAP sensor 210 communicates directly with external system 214 using an ultrasonic, far-field RF, or inductive telemetry link by which the PAP signal is transmitted.

Figure 4:
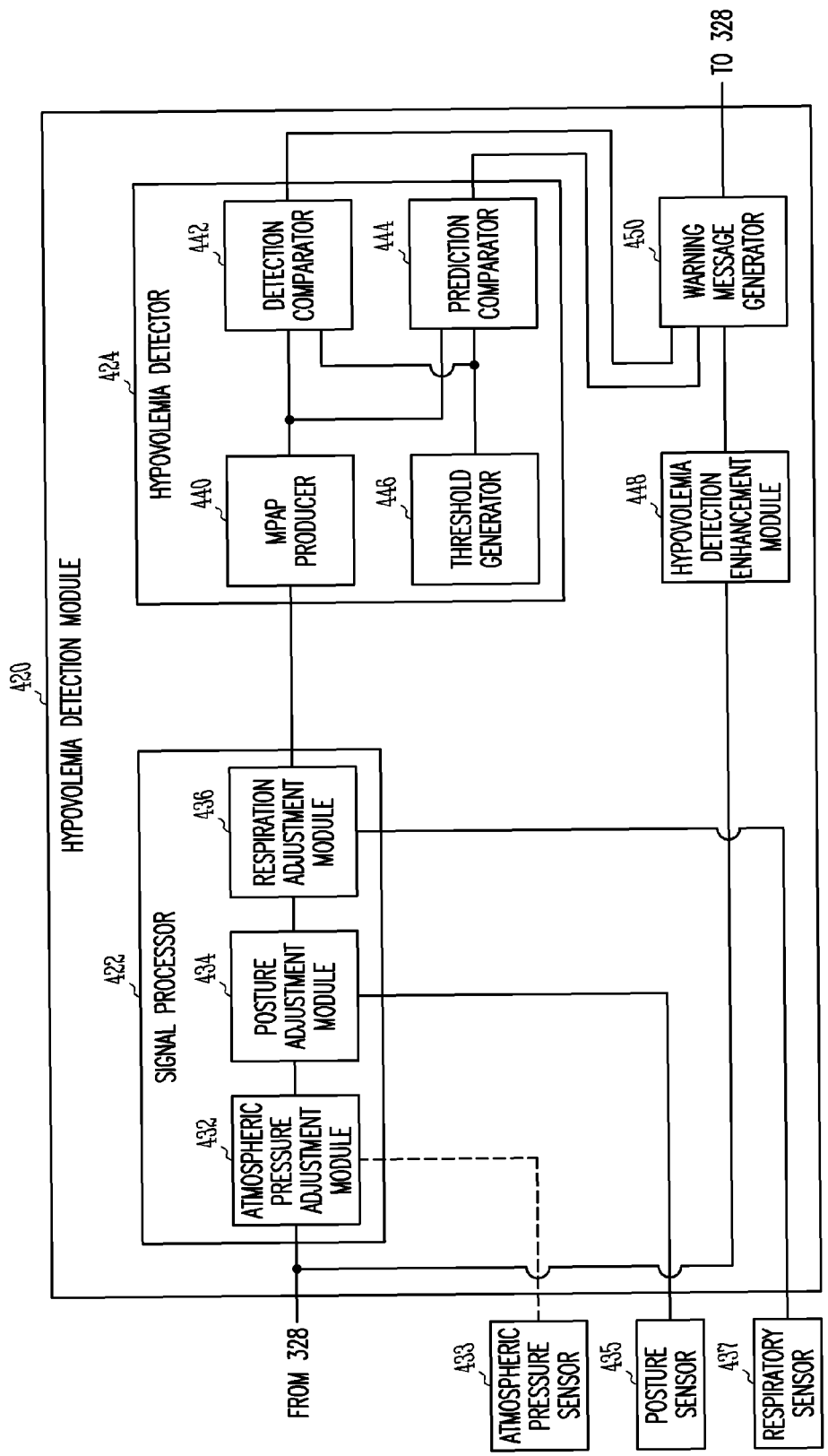
FIG. 4 is a block diagram illustrating an embodiment of portions of a circuit of a hypovolemia detection system of the implantable medical device.

FIG. 4 is a block diagram illustrating an embodiment of portions of the circuit of a hypovolemia detection system of implantable medical device 212. The hypovolemia detection system includes a hypovolemia detection module 420, an atmospheric pressure sensor 433, a posture sensor 435, and a respiratory sensor 437. Hypovolemia detection module 420 is a specific embodiment of hypovolemia detection module 220 and includes a signal processor 422, a hypovolemia detector 424, a hypovolemia detection enhancement module 448, and a warning message generator 450.

Signal processor 422 receives the PAP signal from implant telemetry circuit 328 and processes the PAP signal in preparation for hypovolemia detection. In one embodiment, as illustrated in FIG. 4, signal processor 422 includes an atmospheric pressure adjustment module 432, a posture adjustment module 434, and a respiration adjustment module 436. Atmospheric pressure adjustment module 432 adjusts the PAP signal using an atmospheric pressure sensed by atmospheric pressure sensor 433. In one embodiment, atmospheric pressure sensor 433 is an external pressure calibrator that is to be placed in the vicinity of implantable medical device 212. The external pressure calibrator includes an external barometer to sense the atmospheric pressure and transmits the sensed atmospheric pressure to atmospheric pressure adjustment module 432 via a telemetry link, such as communication link 213. In one embodiment, the external pressure calibrator is a portable device that can be carried by the patient. Posture adjustment module 434 adjusts the PAP signal for effects related to posture of the patient using a posture signal sensed by posture sensor 435. The posture signal is indicative of the posture of the patient. In one embodiment, posture sensor 435 is part of implantable medical device 212. Respiration adjustment module 436 adjusts the PAP signal for effects related to respiratory cycles using a respiratory signal sensed by respiratory sensor 437. The respiratory signal is indicative of respiratory cycles. In one embodiment, respiratory sensor 437 is an impedance sensor that is part of implantable medical device 212 and senses an impedance signal indicative of respiration.

In various embodiments, signal processor 422 includes one or more of atmospheric pressure adjustment module 432, posture adjustment module 434, respiration adjustment module 436, and other functional modules that adjust the PAP signal to remove components of the PAP signal that are considered as noise for the purpose of detecting hypovolemia. In one embodiment, signal processor 422 includes a pruning module that algorithmically prunes predetermined type outlier components from the PAP signal. In one embodiment, signal processor 422 includes a preamplifier and filter circuit and an analog-to-digital converter (ADC). The PAP signal is amplified, filtered, and digitized before being adjusted by one or more of atmospheric pressure adjustment module 432, posture adjustment module 434, and respiration adjustment module 436. In one embodiment, the preamplifier and filter circuit has a gain and a pass-band with a low cutoff frequency and a high cutoff frequency. The gain is in a range of approximately 1 to 10, with approximately 1 being a specific example. The low cutoff frequency is in a range of 0.000001 to 0.1 Hz, with approximately 0.000001 Hz being a specific example. The high cutoff frequency is in a range of 3 to 30 Hz, with approximately 20 Hz being a specific example. The ADC digitizes the PAP signal using a sampling frequency in a range of 10 to 100 Hz, with approximately 50 Hz being a specific example.

Hypovolemia detector 424 receives the processed PAP signal from signal processor 422 and detects hypovolemia using the processed PAP signal. In one embodiment, as illustrated in FIG. 4, hypovolemia detector 424 includes a mean PAP (MPAP) producer 440, a detection comparator 442, a prediction comparator 444, and a threshold generator 446. In various embodiments, hypovolemia detector 424 includes MPAP producer 440 and at least one of detection comparator 442 and prediction comparator 444. MPAP is a specific example of a PAP attribute, and MPAP producer 440 is a specific example of a PAP attribute producer that produces an MPAP as a PAP attribute used for detection of hypovolemia. The MPAP represents a mean amplitude of the PAP signal. In one embodiment, MPAP producer 440 includes a diastolic PAP (DPAP) producer, a systolic PAP (SPAP) producer, and an MPAP calculator. The DPAP producer produces a DPAP that is the smallest value of the PAP during a cardiac cycle. The SPAP producer produces an SPAP that is the largest value of the PAP during the cardiac cycle. In another embodiment, the DPAP and SPAP are measured at predetermined timing intervals after a cardiac event, such as a QRS complex. The cardiac event is identified, for example, using an electrogram sensed by implantable medical device 212 through lead system 208. The MPAP calculator calculates the MPAP as a function of the detected DPAP and SPAP. In a specific embodiment, the MPAP calculator calculates the MPAP using the equation:

$$MPAP = (2 \cdot DPAP + SPAP)/3. \qquad (1)$$

Detection comparator 442 compares the MPAP to a hypovolemia-detection threshold. If the calculated MPAP is below the hypovolemia-detection threshold, detection comparator 442 produces a hypovolemia detection signal indicative of a detection of hypovolemia. In one embodiment, threshold generator 446 stores the hypovolemia-detection threshold as a predetermined number in a range of approximately 5 to 10 mmHg, with approximately 7 mmHg as a specific example. In another embodiment, threshold generator 446 dynamically establishes an MPAP baseline and calculates the hypovolemia-detection threshold as a percentage of the MPAP baseline. The hypovolemia-detection threshold is a dynamically adjusted level that is in a range of approximately 60% to 80% of the MPAP baseline, with approximately 70% of the MPAP baseline being a specific example. The dynamic establishment of the MPAP baseline is discussed below with reference to FIG. 5.

Prediction comparator 444 compares the MPAP to a hypovolemia-prediction threshold. If the calculated MPAP is below the hypovolemia-prediction threshold, prediction comparator 444 produces a hypovolemia prediction signal indicative of an elevated risk of hypovolemia. In one embodiment, threshold generator 446 stores the hypovolemia-prediction threshold as a predetermined number in a range of approximately 7 to 12 mmHg, with approximately 9 mmHg as a specific example. In another embodiment, threshold generator 446 dynamically establishes the MPAP baseline and calculates the hypovolemia-prediction threshold as a percentage of the MPAP baseline. The hypovolemia-prediction threshold is a dynamically adjusted level that is in a range of approximately 70% to 90% of the MPAP baseline, with approximately 80% of the MPAP baseline being a specific example.

Hypovolemia detection enhancement module 448 enhances the detection of hypovolemia using one or more factors related to hypovolemia in addition to the PAP signal. In one embodiment, hypovolemia detection enhancement module 448 receives one or more enhancement signals including one or more of a signal indicative of loss of body weight, a signal indicative of increased heart rate, a signal indicative of postural hypotension, a signal indicative of decreased pulse pressure, a signal indicative of delayed dicrotic notch, a signal indicative of increased hemoglobin, and a signal indicative of increased hematocrit. The reception of each of such one or more enhancement signals increases the likeliness that hypovolemia has occurred. In one embodiment, hypovolemia detection enhancement module 448 receives the one or more enhancement signals from within implantable medical device 212. In another embodiment, hypovolemia detection enhancement module 448 receives the one or more enhancement signals from external system 214 via communication link 213. In another embodiment, hypovolemia detection enhancement module 448 receives the one or more enhancement signals from within implantable medical device 212 and from external system 214 via communication link 213.

Warning message generator 450 produces at least one of an alarm signal and a caution signal. In one embodiment, the one or more of the alarm signal and the caution signal are transmitted to external system 214 via communication link 213. The alarm signal indicates that hypovolemia has occurred. The caution signal indicates an elevated risk of hypovolemia. In one embodiment, warning message generator 450 produces the alarm signal in response to the hypovolemia detection signal and/or the caution signal in response to the hypovolemia prediction signal. In a further embodiment, warning message generator 450 produces the alarm signal and/or the caution signal using the hypovolemia detection signal, the hypovolemia prediction signal, and the one or more enhancement signals.

In a specific embodiment, hypovolemia detection enhancement module 448 uses the one or more enhancement signals to verify each detection of hypovolemia by detection comparator 442 and/or each prediction of hypovolemia by prediction comparator 444. In another specific embodiment, threshold generator 446 adjusts at least one of the hypovolemia-detection threshold and the hypovolemia-prediction threshold using the one or more enhancement signals.

MPAP is discussed as a specific example of the PAP attribute used for detection of hypovolemia. Other specific examples of a PAP attribute include systolic PAP, diastolic PAP, PAP pulse pressure, timing of the dicrotic notch in the PAP signal relative to another PAP feature such as peak systolic PAP, maximum and minimum rates of change in PAP (maximum dPAP/dt and minimum dPAP/dt), systolic PAP time interval, and diastolic PAP time interval. In various embodiments, one or more of such PAP attributes, in addition to or instead of the MPAP, are used for detection of hypovolemia. For example, in addition to the decrease in MPAP, it is know that a decrease in systolic PAP, a decrease in diastolic PAP, a delayed dicrotic notch, and a shortened systolic PAP timer interval are associated with hypovolemia.

Figure 5:
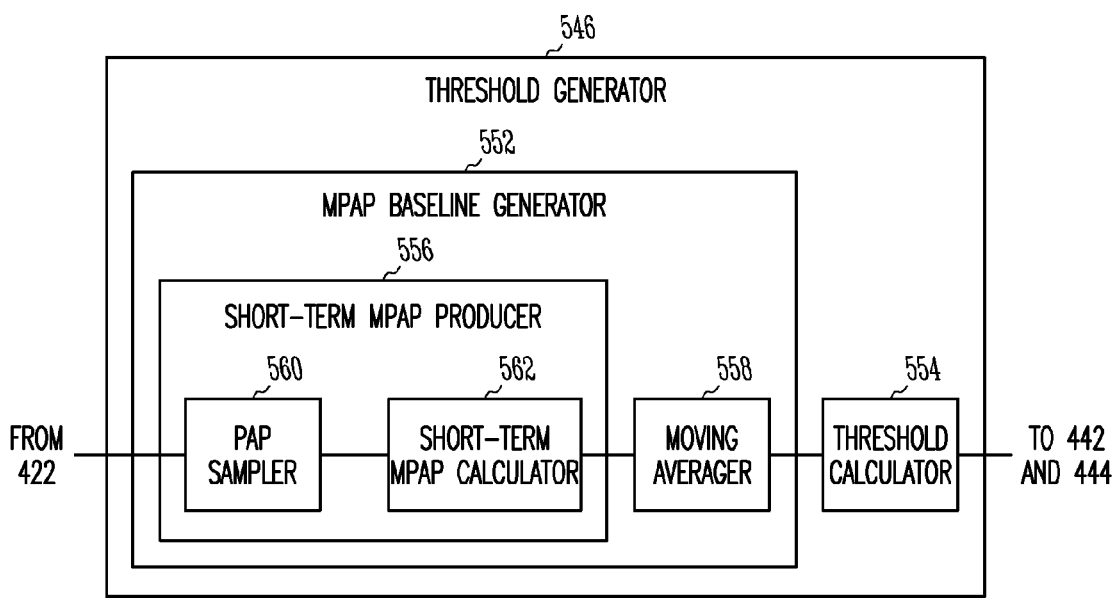
FIG. 5 is a block diagram illustrating an embodiment of portions of a circuit of a threshold generator for generating hypovolemia detection and prediction thresholds.

FIG. 5 is a block diagram illustrating an embodiment of portions of a circuit of a threshold generator 546, which is a specific embodiment of threshold generator 446. Threshold generator 546 includes an MPAP baseline generator 552 that dynamically establishes the MPAP baseline and a threshold calculator 554 that calculates the hypovolemia-detection threshold and/or the hypovolemia-prediction threshold each as a percentage of the MPAP baseline.

MPAP baseline generator 552 includes a short-term MPAP producer 556 and a moving averager 558. Short-term MPAP producer 556 produces a short-term MPAP on a periodic basis using a predetermined period. The short-term MPAP is a short term value or representation of the PAP attribute used for detection of hypovolemia. In one embodiment, the predetermined period is in a range of approximately 2 to 12 hours, with approximately 4 hours being a specific example. Short-term MPAP producer 556 includes a PAP sampler 560 and a short-term MPAP calculator 562. PAP sampler 560 produces a plurality of samples of the PAP signal during the predetermined period. In one embodiment, PAP sampler 560 produces approximately 5-30 samples, with approximately 10 samples being a specific example. In another embodiment, PAP sampler 560 produces the plurality of samples of the PAP signal by sampling the PAP signal on each consecutive respiratory cycle for approximately 30 seconds to 5 minutes, with 1 minute being a specific example. Short-term MPAP calculator 562 calculates the short-term MPAP by averaging the samples of the plurality of samples of the PAP signal. Moving averager 558 produces the MPAP baseline by calculating a moving average of a plurality of short-term MPAPs on the periodic basis. That is, after short-term MPAP calculator 562 calculates each new short-term MPAP, moving averager 558 updates the MPAP baseline by calculating a moving average of short-term MPAPs including that new short-term MPAP. In one embodiment, moving averager 558 updates the MPAP baseline by calculating a moving average of short-term MPAPs produced over a predetermined duration in a range of approximately 5 to 45 days, with approximately 30 days being a specific example.

Figure 6:
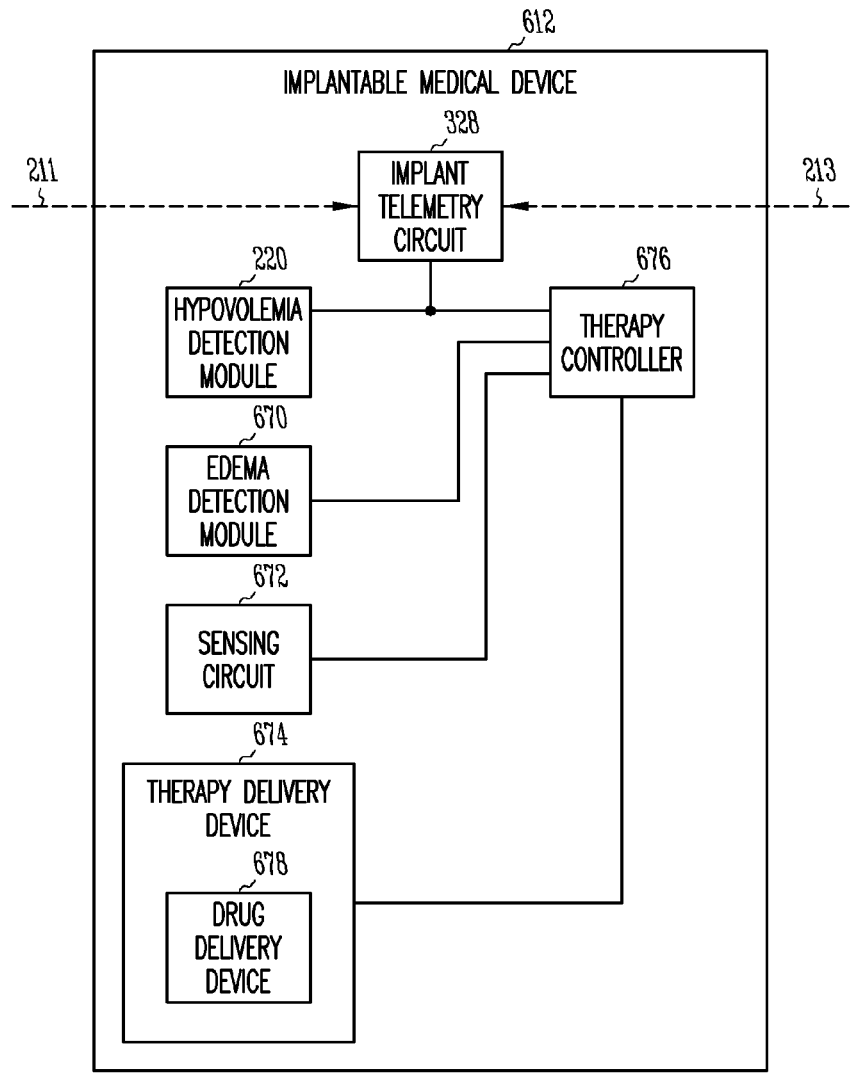
FIG. 6 is a block diagram illustrating an embodiment of portions of a circuit of the implantable medical device.

FIG. 6 is a block diagram illustrating an embodiment of portions of a circuit of an implantable medical device 612, which is a specific embodiment of implantable medical device 212. Implantable medical device 612 includes implant telemetry circuit 328, hypovolemia detection module 220, an edema detection module 670, a sensing circuit 672, a therapy delivery device 674, and a therapy controller 676.

Edema detection module 670 receives a physiological signal indicative of a level of fluid retention in body 202 and detects edema from that physiological signal. When the edema is detected, edema detection module 670 produces an edema detection signal indicative of the detection of edema. In one embodiment, edema detection module 670 includes a pulmonary edema detector that produces a pulmonary edema detection signal indicative of a detection of pulmonary edema. An example of a pulmonary edema detector is discussed in U.S. patent application Ser. No. 10/897,856, entitled "METHOD AND APPARATUS FOR MONITORING HEART FAILURE PATIENTS WITH CARDIOPULMONARY COMORBIDITIES," filed Jul. 23, 2004, assigned to Cardiac Pacemakers, Inc., which is incorporated herein by reference in its entirety.

Sensing circuit 672 senses one or more signals, such as one or more electrogram signals, for therapy control purposes. Therapy delivery device 674 delivers one or more therapies. In one embodiment, as illustrated in FIG. 6, therapy delivery device 674 includes a drug delivery device 678 that delivers one or more diuretic agents. In various embodiments, therapy delivery device 674 includes one or more of a pacing circuit, a cardioversion/defibrillation circuit, a neural stimulation circuit, a drug delivery device, and a biological therapy device. Therapy controller 676 controls the delivery of the one or more therapies using the hypovolemia detection signal produced by hypovolemia detection module 220, the edema detection signal produced by edema detection circuit 670, and/or the one or more signals sensed by sensing circuit 672. In a further embodiment, therapy controller 676 includes a command receiver to receive one or more user commands from external system 214 via communication link 213. Therapy controller 676 controls the delivery of the one or more therapies using the hypovolemia detection signal, the edema detection signal, the one or more signals sensed by sensing circuit 672 and/or the one or more user commands.

In a specific embodiment, implantable medical device 612 provides therapy for a heart failure patient. Therapy controller 676 controls a drug therapy treating decompensation using feedback control. Edema detection module 670 detects an edema indicative of the decompensation. In response to the edema detection signal produced by edema detection module 670, therapy controller 676 causes drug delivery device 678 to release a diuretic agent. Hypovolemia detection module 220 detects a hypovolemia indicative of an over dose of the diuretic agent. In response to the hypovolemia detection signal produced by hypovolemia detection module 220, therapy controller 676 stops drug delivery device 678 from further release of the diuretic agent.

While implantable medical device 612 is discussed as a specific example, control of therapy using hypovolemia detection and edema detection according to the present subject matter is not limited to control of therapy delivery using an implantable medical device. In one embodiment, signals representative of detection of edema and detection of hypovolemia are produced by an implantable medical device and telemetered to an external system for controlling one or more therapies treating heart failure decompensation. In a specific embodiment, the one or more therapies include at least a drug therapy using a diuretic agent. The heart failure patient starts receiving the diuretic agent in response to a detection of edema and stops receiving the diuretic agent in response to a detection of hypovolemia. In another embodiment, signals representative of detection of edema and detection of hypovolemia are produced by an implantable medical device and communicated to another implantable medical device for controlling one or more therapies for heart failure.

Figure 7:
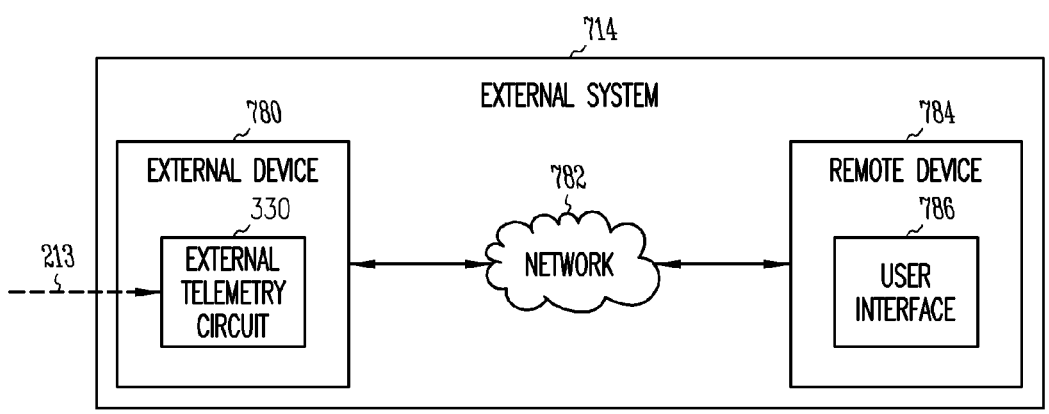
FIG. 7 is a block diagram illustrating an embodiment of an external system communicating with the implantable medical device.

FIG. 7 is a block diagram illustrating an embodiment of an external system 714, which is a specific embodiment of external system 214. As illustrated in FIG. 7, external system 714 is a patient management system including an external device 780, a telecommunication network 782, and a remote device 784. External device 780 is placed within the vicinity of the implantable medical device 212 and includes external telemetry system 330 to communicate with the implantable medical device 212 via telemetry link 213. Remote device 784 is in one or more remote locations and communicates with external device 780 through network 782, thus allowing the user to monitor and treat the patient from a distant location and/or allowing access to various treatment resources from the one or more remote locations. In one embodiment, remote device 784 includes a user interface 786. User interface 786 includes a presentation device and a user input device. In one embodiment, external system 714 receives signals such as the hypovolemia detection signal, the hypovolemia prediction signal, the edema detections signal, the alarm signal, and the caution signal discussed above. The presentation device presents such signals in various forms to inform the user of the patient's condition that may require an urgent medical intervention. The user input device receives one or more user commands to start, stop, or adjust the delivery of one or more therapies from an implantable medical device.

Figure 8:
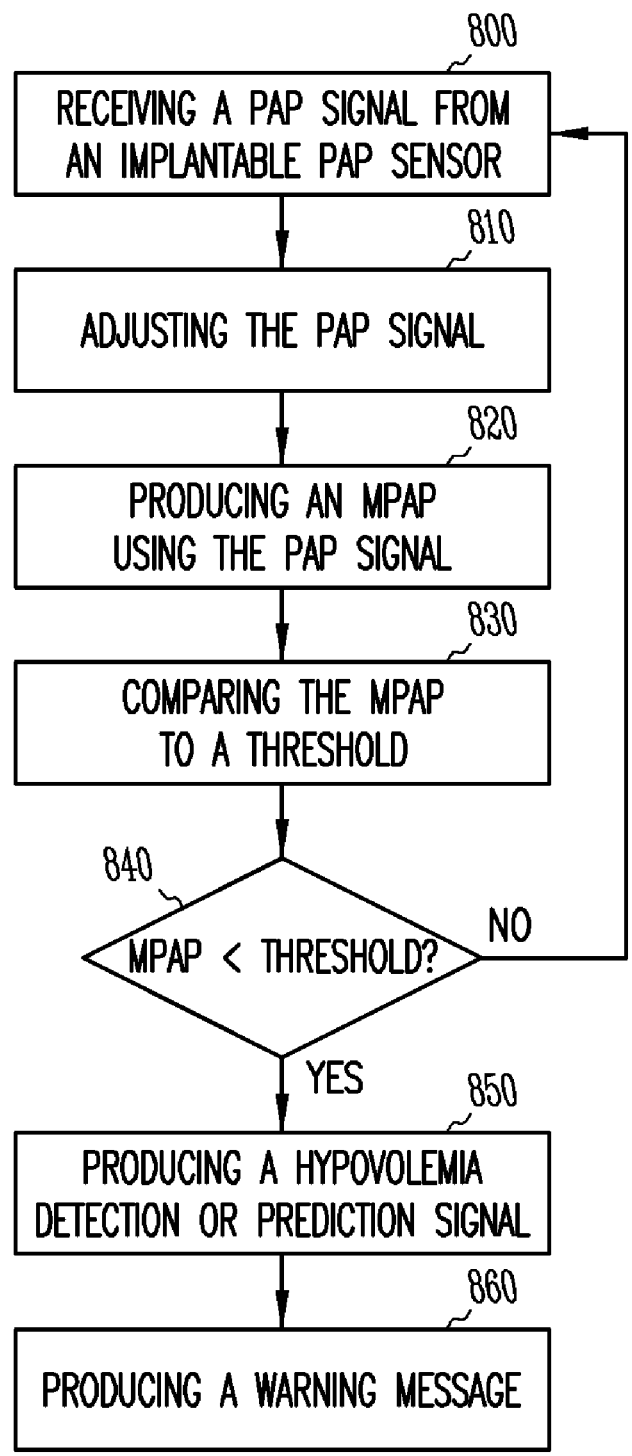
FIG. 8 is a flow chart illustrating an embodiment of a method for detecting hypovolemia.

FIG. 8 is a flow chart illustrating an embodiment of a method for detecting hypovolemia. In one embodiment, the method is performed by system 100 or system 200, including their various embodiments discussed in this document.

A PAP signal is received from an implantable PAP sensor at 800. In one embodiment, the implantable PAP sensor is a pressure sensor configured for placement within the pulmonary artery of a patient to sense the PAP. In another embodiment, the implantable PAP sensor includes a physiological sensor that senses a physiological signal indicative of the PAP.

The PAP signal is adjusted at 810, to remove components of the PAP signal that are considered as noise for hypovolemia detection purposes. Examples of such components to be removed include components attributed to atmospheric pressure, posture of the patient, and respiratory cycles. In one embodiment, an atmospheric pressure is sensed using an external pressure calibrator, and the PAP signal is calibrated for the atmospheric pressure. In one embodiment, a posture signal is sensed using a posture sensor implanted in or attached to the patient, and the PAP signal is adjusted using the posture signal to remove effects related to the patient's posture. In one embodiment, a respirator signal is sensed using a respiratory sensor implanted in or attached to the patient, and the PAP signal is adjusted using the respiratory signal to remove effects related to respiratory cycles.

An MPAP is produced using the PAP signal at 820. The MPAP is specifically discussed as an example illustrating detection of hypovolemia using a PAP attribute. In one embodiment, a DPAP is detected from the PAP signal during a diastolic phase, and an SPAP is detected from the PAP signal during a systolic phase. The MPAP is calculated using the DPAP and the SPAP. In a specific embodiment, the MPAP is calculated using Equation (1) given above.

The MPAP is compared to a threshold at 830. In one embodiment, the MPAP is compared to one or more of a hypovolemia-detection threshold indicative of an occurrence of hypovolemia and a hypovolemia-prediction threshold indicative of an elevated risk of hypovolemia. In one embodiment, the hypovolemia-detection threshold and the hypovolemia-prediction threshold are each a predetermined pressure level. In another embodiment, the hypovolemia-detection threshold and the hypovolemia-prediction threshold are each a percentage of an MPAP baseline. In another embodiment, the hypovolemia-detection threshold and the hypovolemia-prediction threshold are each a predetermined pressure level below the MPAP baseline. The MPAP baseline is established based on the PAP signal sensed from the patient and periodically updated. To update the MPAP baseline, a plurality of samples of the PAP signal is produced on a periodic basis using a predetermined period. A short-term MPAP is calculated by averaging the samples of the plurality of samples of the PAP signal on the periodic basis. Each time after a new short-term MPAP is calculated, the MPAP baseline is updated by calculating a moving average of a plurality of the short-term MPAPs including the new short-term MPAP.

If the MPAP is below the threshold at 840, a hypovolemia detection or prediction signal is produced at 850. In one embodiment, the MPAP is compared to both the hypovolemia-detection threshold and the hypovolemia-prediction at 840, a hypovolemia detection signal is produced at 850 if the MPAP is below the hypovolemia-detection threshold, or a hypovolemia prediction signal is produced at 850 if the MPAP is below the hypovolemia-prediction threshold. In one embodiment, the detection of the hypovolemia is enhanced using one or more enhancement signals. Examples of such enhancement signals include a signal indicative of loss of body weight, a signal indicative of increased heart rate, a signal indicative of an increased respiratory rate, a signal indicative of postural hypotension, a signal indicative of decreased pulse pressure, a signal indicative of delayed dicrotic notch, a signal indicative of increased hemoglobin, and a signal indicative of increased hematocrit. These enhancement signals each indicates an increased likeliness that hypovolemia has occurred or will occur.

A warning message is produced at 860. The warning message is produced based on at least one of the hypovolemia detection signal, the hypovolemia prediction signal, and the one or more enhancement signals. Examples of the warning message include an alarming signal indicative of an occurrence of the hypovolemia and a caution signal indicative of an elevated risk of hypovolemia. Such a warning message warns the patient to seek medical assistance and/or warns a physician or other caregiver that the patient may be indicated for urgent medical intervention.

Figure 9:
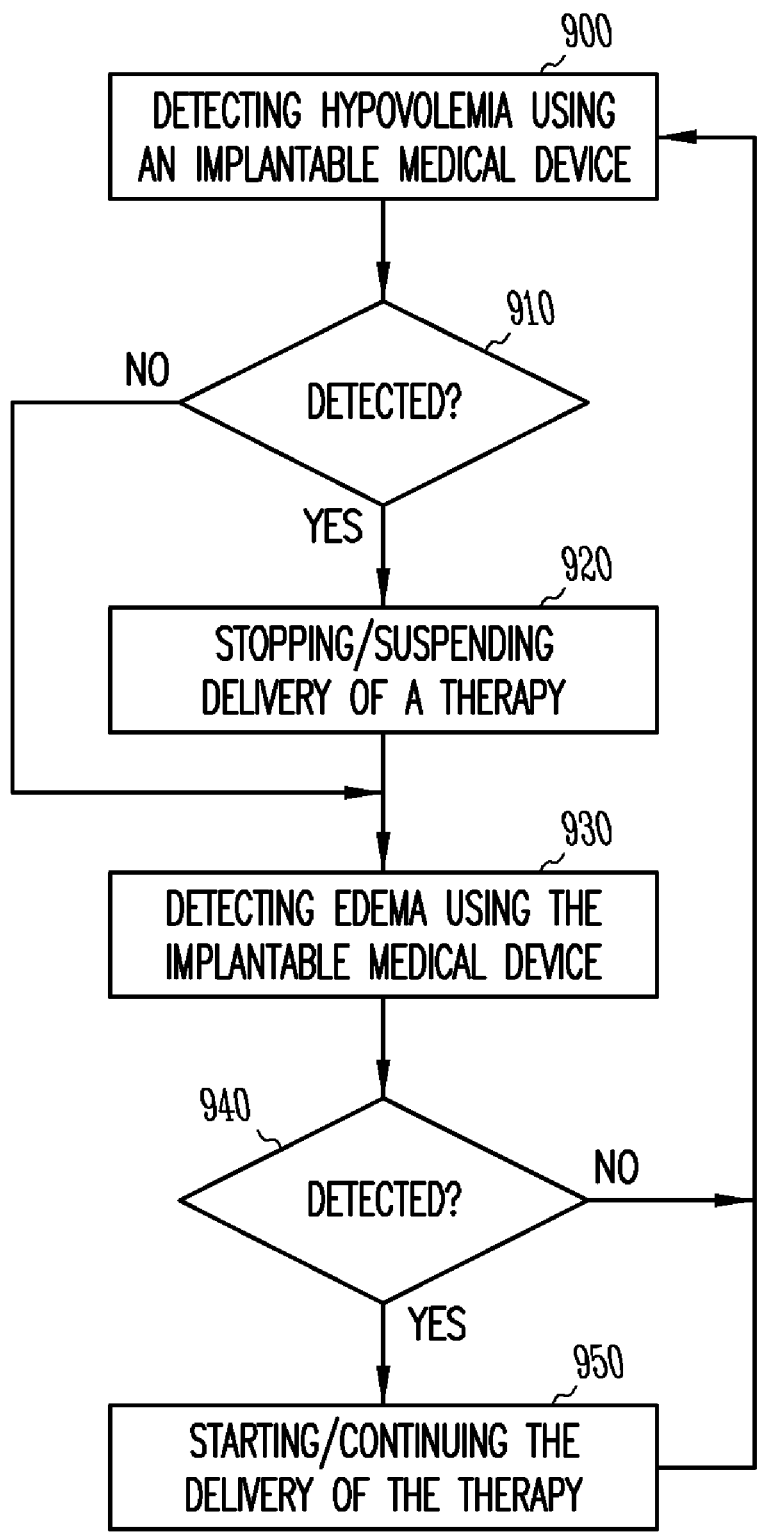
FIG. 9 is a flow chart illustrating an embodiment of a method for controlling a therapy using hypovolemia and edema detection.

FIG. 9 is a flow chart illustrating an embodiment of a method for controlling a therapy using hypovolemia and edema detection. In one embodiment, the therapy is applied to a heart failure patient who has experienced decompensation or is likely to experience decompensation. In a specific embodiment, the therapy includes delivery of one or more diuretic agents. In one embodiment, the method is performed by implantable medical device 612.

An implantable medical device detects hypovolemia at 900. In one embodiment, the implantable medical device receives a physiological signal indicative of circulatory blood volume sensed by a physiological sensor and detects hypovolemia from that physiological signal. In a specific embodiment, the physiological signal is a PAP signal sensed by an implantable pressure sensor placed within the pulmonary artery.

If the hypovolemia is detected at 910, delivery of the therapy is stopped or suspended at 920. If the hypovolemia is not detected at 910, the implantable medical device detects edema at 930. In one embodiment, the implantable medical device receives another physiological signal indicative of a fluid retention in one or more locations in the patient by another physiological sensor and detects edema from that physiological signal. In a specific embodiment, pulmonary edema is detected. An example of pulmonary edema detection is discussed in U.S. patent application Ser. No. 10/897, 856.

If the edema is detected at 940, delivery of the therapy is started or continued at 950. If the edema is not detected at 940, the implantable medical device continues to detect hypovolemia at 900. Steps 900-950 are repeated while the heart failure patient is treated with the therapy.

FIGS. 10-25 illustrate exemplary embodiments of apparatus and method for delivering, positioning, and anchoring an implantable PAP sensor. These examples are also discussed in U.S. patent application Ser. No. 11/216,738 entitled "DEVICES AND METHODS FOR POSITIONING AND ANCHORING IMPLANTABLE SENSOR DEVICES," filed on Aug. 31, 2005, assigned to Cardiac Pacemakers, Inc., which is incorporated herein by reference in its entirety.

Figure 10:
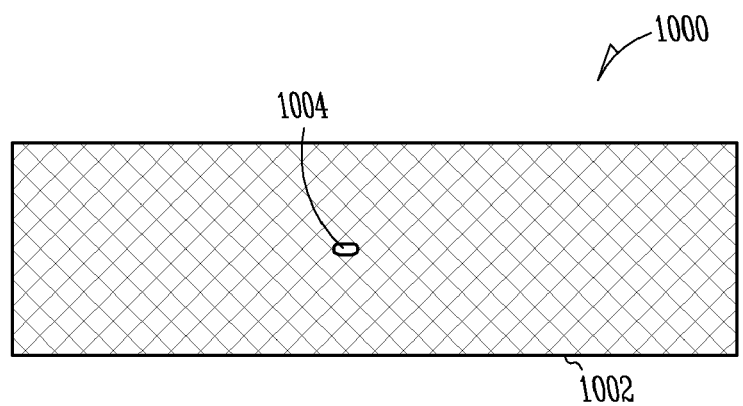
FIG. 10 illustrates a sensor anchoring device in accordance with one embodiment of the present invention.
Figure 11:
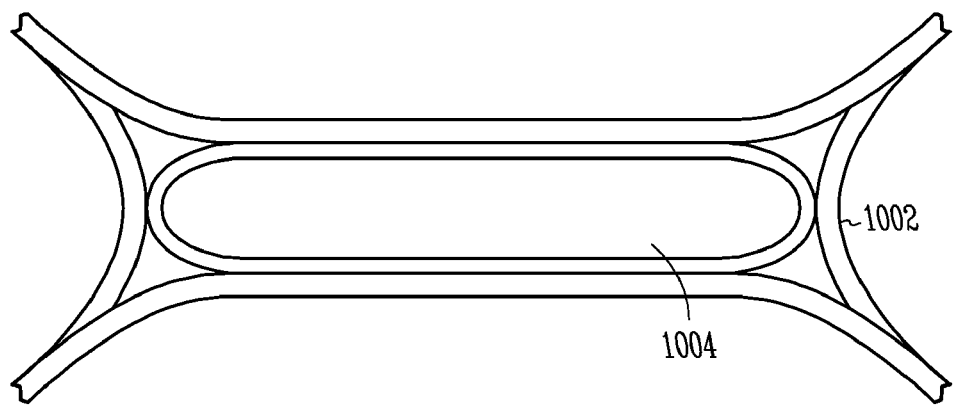
FIG. 11 is a top view of a section of the sensor anchoring device of FIG. 10 in which a sensor is placed.

FIG. 10 shows one embodiment of a physiologic sensor anchoring system 1000. In accordance with the illustrated embodiment, anchoring system 1000 comprises a stent-like structure 1002 carrying a physiologic parameter sensor 1004 (e.g., pressure sensor). The stent-like structure generally has a tubular shape like a stent, and is adapted to carry the sensor 1004 into a bodily vessel. In this particular embodiment, the physiologic parameter sensor 1004 is embedded in a mesh structure of the stent-like structure 1002, as is illustrated in a close-up view in FIG. 11.

Figure 12:
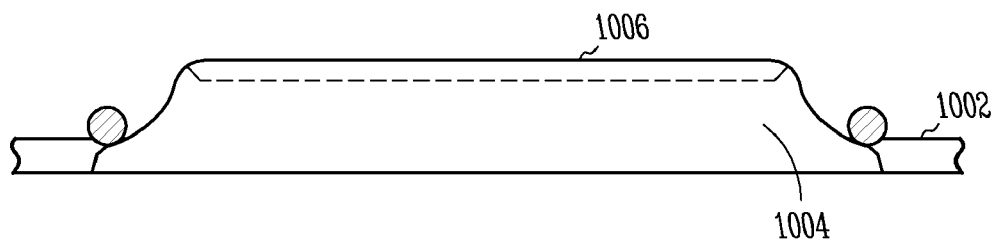
FIG. 12 is a side view of the sensor anchoring device section and sensor illustrated in FIG. 11.

The sensor 1004 may be secured to and carried by the stent-like structure 1002 in any number of ways. For example, as illustrated in FIG. 12, sensor 1004 can rest in a recessed diaphragm 1006 positioned in the stent 1002. In alternative embodiments, sensor 1004 can be secured within the stent using other securing mechanisms, such as adhesives, welding techniques, or the like. In addition, sensor 1004 is configured to communicate with implantable medical devices (IMDs), such as cardiac rhythm management device, and/or devices outside of a patient body. Examples of the sensors, sensor configurations, and communication systems and methods discussed in this document are discussed in more detail in U.S. patent application Ser. No. 10/943,626 entitled "SYSTEMS AND METHODS FOR DERIVING RELATIVE PHYSIOLOGIC PARAMETERS," U.S. patent application Ser. No. 10/943,269 entitled "SYSTEMS AND METHODS FOR DERIVING RELATIVE PHYSIOLOGIC PARAMETERS USING AN EXTERNAL COMPUTING DEVICE," U.S. patent application Ser. No. 10/943,627 entitled "SYSTEMS AND METHODS FOR DERIVING RELATIVE PHYSIOLOGIC PARAMETERS USING A BACKEND COMPUTING SYSTEM," and U.S. patent application Ser. No. 10/943,271 entitled "SYSTEMS AND METHODS FOR DERIVING RELATIVE PHYSIOLOGIC PARAMETERS USING AN IMPLANTED SENSOR DEVICE," and filed by Abhi Chavan et al., all assigned to Cardiac Pacemakers, Inc., which are incorporated herein by reference in their entirety and are collectively referred to as the "Physiologic Parameter Sensing Systems and Methods Patents" in this document.

In other embodiments, anchoring system 1000 may be used for the placement of IMDs with therapeutic functions such as actuating devices. For example, common actuators include, but are not limited to, an ultrasound sensor and a drug delivery pod. In some embodiments, anchoring system 1000 may be used to place a plurality of sensors, actuators, or a combination of sensors and actuators. Placement of multiple sensors and/or actuating devices throughout the body can allow for a more comprehensive therapeutic and diagnostic system, but multiple sensors and/or actuating devices are not required.

By using a stent-like anchoring structure, a sensor or any IMD can be anchored and secured in any part of the vascular system. In one particular embodiment, the stent-structure can be a balloon expandable stent, which can be placed in the vascular system using known catheterization techniques. For example, in one embodiment, the stent-structure can be positioned and secured in the pulmonary artery using techniques similar to a Swan Ganz technique, or other similar catheterization techniques. In this particular embodiment, when the stent-like anchoring mechanism 1002 is expanded, sensor 1004 will be place next to, or in close proximity to the vessel wall, allowing the sensor to obtain measurements from next to the vessel wall, which can be beneficial in many situations. As one skilled in the art will appreciate, for anchoring sensors in large cavities and/or arteries, stent-like anchoring mechanism 1002 may be larger than a traditional stent device. However, the device configuration can be similar.

A balloon deployable stent can be made of stainless steel, cobalt chromium, nitinol, and the like. The material composition of the stent may be determined based on a variety of factors. For example, a stent placed in an artery in a patient's neck typically has a shape-memory because the stent may be deformed by exogenous pressures. In contrast, a stent positioned in the heart will have the protection of the patient's rib cage to help protect the stent from outside forces. Thus, it is not as important for a stent that is positioned in the heart to be made of a memory retaining material.

The stent is typically located on the outside of the balloon. As such, while inflating the balloon the stent expands. In many instances, it is desirable to activate and test the sensor during the placement, or positioning, phase. However, one potential problem with the balloon expandable stent approach is that while the balloon is inflated, the blood flow through the artery may be reduced or completely blocked. Hence, the sensor may not be able to provide an accurate measurement during placement. In addition, if the procedure is complicated, positioning of the sensor or actuator may take more time than the patient can safely be with reduced blood flow, or without blood flow entirely, in that area.

The balloon composed of a semi-permeable or permeable membrane. For example, the balloon may have holes, or paths, which allow the blood to flow. Another possible solution is for the balloon to be in a shape, such as a cloverleaf shape, that provides pockets through which blood can continue to flow while the balloon is inflated. A cloverleaf shape will not completely block the artery, as blood will be able to flow between the pedals of the clover shaped balloon. These techniques allow the sensor to be activated and tested during the positioning of the device, some benefits of which are discussed below.

In some embodiments, by using a stent-like anchoring structure, a physician can perform two functions at once; i.e., use a stent to expand and support a vessel while placing a physiologic parameter sensor in a desired location. Also, using a stent-like structure can have additional benefits, such as, for example: (1) the stent structure, if coated with one or more drugs to minimize inflammation, can help inhibit the long term inflammation of artery or vessel tissue, which can occur when other anchoring techniques are used; (2) when using a self expanding stent, the sensor can be tested prior to anchoring, and if there are problems with the sensor, it can be retracted prior to deploying the stent-like anchoring device; (3) the controlled deployment of the stent-structure can prevent incorrect anchoring within the artery or vessel, which can lead to serious thrombolytic effects; and (4) the stent-like structure might assist in evoking a limited tissue growth response over the sensor anchor, thus holding the sensor in place (a further embodiment of this concept is discussed in more detail below.

In accordance with these embodiments of the invention, the specific type of stent and its anchoring location is not limited. For example, the stent-like structure can be made of titanium, stainless steel, nitinol, or some other suitable bio-compatible material, and the stent-like structure design is not limited to any particular configuration. Further, as discussed above, the stent-like structure can be place in any part of the vascular system, including but not limited to, any venous or aortic blood vessel, the pulmonary artery, blood vessels distal from the heart, or any cardiac separating or enclosing wall (e.g., the atrial septum). In addition, as discussed above, the sensor can be configured to measure any physiologic parameter value, including any physical, chemical or biologic property or parameter. Finally, in one embodiment, the stent-like structure and/or sensor can be coated with drugs or other materials, which can reduce thrombolytic or inflammatory effects, promote fibrosis, or the like.

Figure 13:
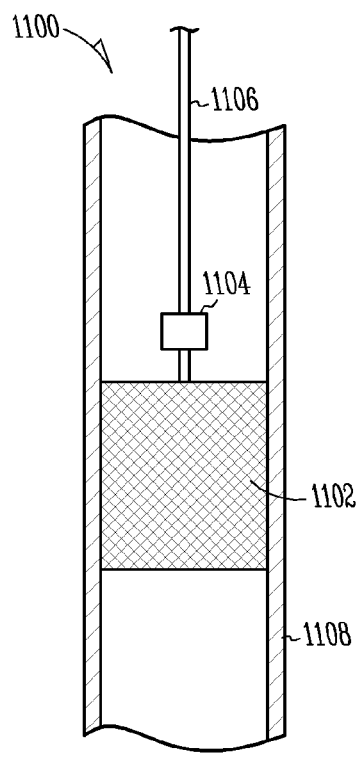
FIG. 13 is a cross-sectional view of one embodiment of a sensor anchoring device positioned within a bodily cavity.

FIG. 13 illustrates another embodiment of a physiologic parameter sensor and anchoring system 1100. In the embodiment illustrated in FIG. 13, system 1100 comprises an anchoring device 1102, a physiologic parameter sensor 1104, and one or more leads 1106 attached to sensor 1104. In this particular embodiment, anchoring device 1102 comprises a stent-like anchoring device, similar to the stent-like device discussed above. In FIG. 13, anchoring device 1102 is shown expanded and anchored in a blood vessel 1108. Again, as discussed above, vessel 1108 can be any blood vessel within the body. In addition, anchoring device 1102 is not limited to stent-like structure. Other anchoring devices, such as the devices discussed below, also can be used. Further, embodiments of the present invention are not limited to obtaining physiologic measurements within blood vessels.

In this particular embodiment, sensor 1104 is attached or connected to lead 1106, and lead 1106 is further attached to anchoring device 1102. Thus, the purpose of anchoring device 1102 is to hold the sensor 1104 and lead 1106 configuration in a particular location in a vessel or other bodily cavity. As discussed in more detail in the Physiologic Parameter Sensing Systems and Methods Patents, lead 1106 can facilitate communication between sensor 1104 and an IMD, such as a cardiac rhythm management IMD. Lead 1106 can carry sensor measurements from sensor 1104 to the IMD, as well as therapy and/or other information from the IMD to the sensor 1104. Further, lead 1106 can be any suitable biocompatible lead (e.g., silicone, polyurethane, etc.) currently known or later developed.

Figure 14:
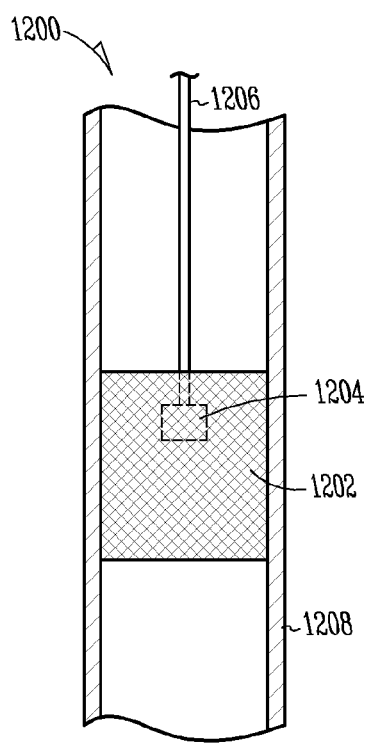
FIG. 14 is a cross-section view of another embodiment of a sensor anchoring device positioned within a bodily cavity.

FIG. 14 shows yet another embodiment of a physiologic parameter sensor and anchoring system 1200. In the embodiment illustrated in FIG. 14, system 1200 also comprises an anchoring device 1202, a physiologic parameter sensor 1204, and one or more leads 1206 attached to sensor 1204 and/or anchoring device 1202. According to various embodiments, the leads 1206 may be a conductor, such as a braided cable. Examples of material from which the tether may be formed include, but are not limited to, MP35N, stainless steel, and other standard lead conductors. According to some embodiments, the diameters of the leads 1206 typically range from 0.006 to 0.009 inches. In other embodiments, the diameters of the leads have a much larger range.

As with the embodiment illustrated in FIG. 13, anchoring device 1202 comprises a stent-like anchoring device, but other anchoring devices can be used. In FIG. 14, anchoring device 1202 is shown expanded and anchored in a blood vessel 1208. Again, as discussed above, vessel 1208 can be any blood vessel within the body, or any other bodily cavity, and embodiments of the present invention are not limited to obtaining physiologic measurements within blood vessels.

In this particular embodiment, sensor 1204 is connected to anchoring device 1202. Lead 1206 is attached to sensor 1204, and can be configured to communicate information to/from an IMD (e.g., a cardiac rhythm management IMD), as discussed in more detail in the Physiologic Parameter Sensing Systems and Methods Patents referenced above. For example, lead 1206 can carry sensor measurements from sensor 1204 to the IMD, as well as therapy and/or other information from the IMD to the sensor. Thus, one function of anchoring device 1202 is to hold the sensor 1204 in a particular location in a vessel or other bodily cavity, and one function of lead 1204 is to facilitate communication with the IMD.

Figure 15:
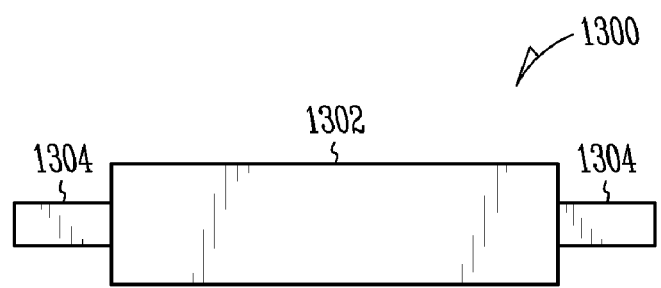
FIG. 15 is a view of one embodiment of a sensor device that can be anchored in a bodily cavity in accordance with one embodiment of the invention.

FIG. 15 illustrates one embodiment of a sensor device 1300 that can be positioned and anchored within a bodily cavity, such as a blood vessel, or the like. In the embodiment illustrated in FIG. 15, sensor device 1300 comprises a sensing mechanism (e.g., pressure sensor, circuitry, etc.) 1302 and one or more fins or extensions 1304 that can facilitate the anchoring of sensor device 1300 in a bodily vessel. In addition to fins 1304, the sensor 1300 may have a Dacron skirt (not shown) that promotes fibrous ingrowth/overgrowth. In one embodiment, the skirt is similar to those used on myocardial leads. By the time the stent bio-absorbs, such a skirt will have securely grown to the wall of the vessel. The Dacron skirt can be positioned on the bottom of the sensor 1300, but can also extend beyond the dimensions of the sensor 1300.

With regard to embodiments that include outwardly extending fins 1304, the stent-like structure 1306 may include sleeves (not shown) formed on a wall of the stent-like structure 1306 and configured for receiving and holding the fins 1304. Thus, the sensor device 1300 can be attached to the stent-like structure 1306 by sliding the fins 1304 into corresponding sleeves of the stent-like structure 1306. The sleeves may be configured to allow for tissue fibrosis, thereby enabling gradual tissue growth over the fins 1304 to secure the sensor device 1300 to a wall of the bodily vessel 1308.

Figure 16:
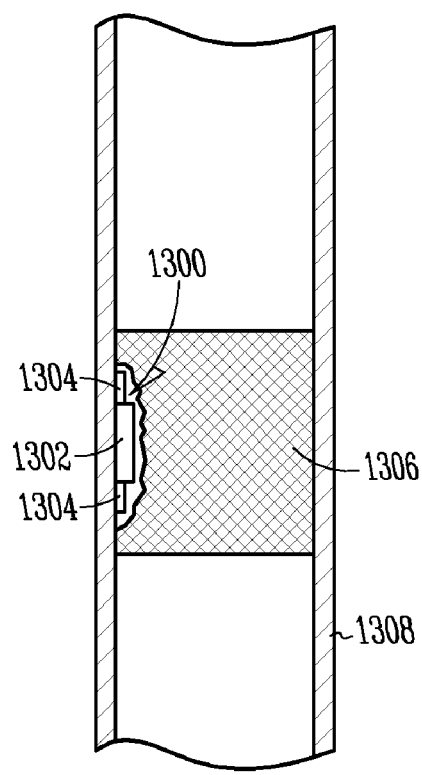
FIG. 16 is a cross-section view showing the sensor device of FIG. 15 being held in place in a bodily cavity by another embodiment of a sensor anchoring device.

According to some embodiments, the extension beyond the dimensions of the sensor 1300 is similar to the configuration in epicardial (EPI) leads. As shown in FIG. 16, sensor device 1300 can be positioned within the bodily vessel (e.g., blood vessel 1308 in FIG. 16), and initially anchored or held in place using an expandable stent-like structure 1306. As discussed above, stent-like structure 1306 can be any suitable stent device or other anchoring device currently known or later developed. In this particular embodiment, however, stent-like structure 1306 is bio-absorbable, and thus, will dissolve within a given time period (e.g., about 6-8 months).

In accordance with this particular embodiment, and as illustrated in FIG. 16, sensor device 1300 is connected to anchoring device 1306, so that sensor device 1300, and in particular, the one or more fins 1304, are positioned near the wall of vessel 1308. The device 1300 may be connected to the anchoring device 1306 by a tether, a mold, dissolvable sutures, and the like. In any event, by placing the fins or extensions 1304 near the vessel wall, tissue from the vessel will fibrose or grow over the fins 1304, securing the sensor device 1300 in the vessel. As one skilled in the art will appreciate, it may take time for fibrous tissue to form over extensions 1304. As such, a relatively slow dissolving bio-absorbable anchoring device 1306 is typically used to initially secure sensor device 1300 in place. As one skilled in the art will appreciate, the vessel tissue typically will fibrose over extensions 1304 within a period between about 3 months and 6 months, which is typically before anchor device 1306 will completely dissolve.

In one embodiment, sensor device 1300, including extensions 1304 are formed from a bio-compatible material, such as stainless steel, titanium, nitinol, or some other bio-compatible material. In some embodiments, sensor mechanism 1302 and extensions 1304 are formed of the same material. In other embodiments, sensor mechanism 1302 and extensions can be formed of different materials. In yet other embodiments, extensions 1304 can comprise dacron, nylon or other bio-compatible graphs or patches, making it easier for tissue to adhere thereto. As one skilled in the art will appreciate, any number of extension 1304 can be used, and extensions 1304 can be any suitable size, shape and/or material. Thus, embodiments of the present invention are not limited to any particular material or extension 1304 configuration illustrated and/or described herein. Further, in still other embodiments, sensor device 1300 can be coated with one or more drugs that might help reduce inflammation and/or encourage or facilitate tissue fibrosis. Such drugs are currently known in the art.

In some embodiments, a fabric, such as Gore-Tex® (gore), may be placed between the stent and the sensor or actuator. The placement of this fabric facilitates in keeping the tissue from attaching to the sensor itself and only allows the tissue to grow around the stent. As such, the sensor, actuator, or some part of the circuitry such as the battery, may be detached, removed or replaced during a surgical procedure at a later time. For example, in FIG. 10 the sensor or actuator 1002 may be removed, replaced, and reattached to anchoring mechanism 1002 with a new sensor or actuator. In some embodiments, gore may also be used to cover both sides of the stent. In these embodiments, the stent is sandwiched between two layers of gore and the physical expansion of the stent holds the device in place, even with the gore sheets on either side. However, since tissue can not grow through the stent due to the gore, the entire stent may be more easily removed at a later time.

Figure 17:
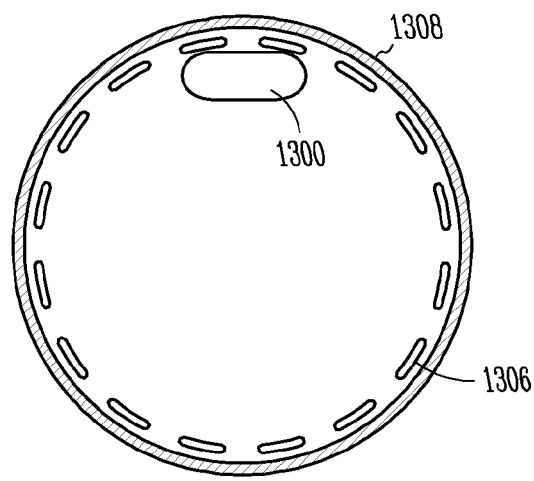
FIG. 17 is an axial view showing the sensor device of FIG. 15 being held in place in a bodily cavity in accordance with one embodiment of an anchoring device.

One embodiment, as illustrated in FIG. 16, has a sensor device 1300 placed within the anchoring device 1306. FIG. 17 shows an axial view of this embodiment. However, the anchoring device 1306 may be placed on one side of the sensor device 1300. Or, an anchoring device may be attached to both sides of the sensor or actuator's extensions or fins 1304. This type of dual attachment of the sensor device 1300 to one or more anchoring devices 1306 may help facilitate more accurate final positioning of the sensor as both sides of the device may be anchored in place before the tissue grows around the device.

Figure 18:
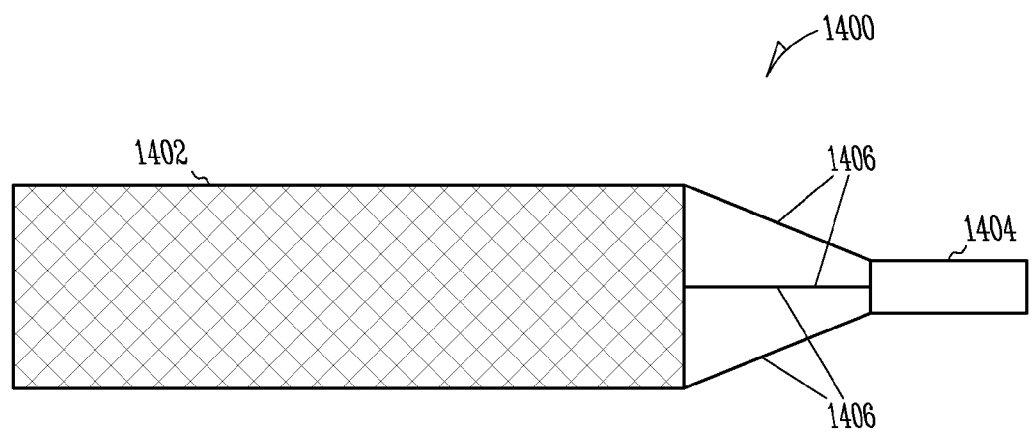
FIG. 18 is a view of another embodiment of a sensor anchoring device.

FIG. 18 shows yet another embodiment of an IMD anchoring system 1400. In this particular embodiment, anchoring system 1400 comprises an anchoring device 1402, a sensor 1404, and one or more connection structures 1406 for connecting sensor 1404 to anchoring device 1402. In this particular embodiment, connection structures 1406 are configured to secure sensor 1404 so that the sensor will reside near the middle of a blood vessel. By placing the sensor 1404 near the middle of the vessel, the sensor 1404 will reside in the predominant blood flow that occurs in the middle of the vessel, avoiding edge effects, such as slower blood flow, dead zones, and perhaps clotting issues.

In one embodiment, anchoring device 1402 can include a stent-like structure, as discussed above. Further, connection structures 1406 can comprise any structural configuration that will secure sensor 1404 in a desired location. For example, connection structures 1406 can comprise one or more strut-type structures configured to hold sensor 1404 in front of, or in back of anchoring device 1402. In this particular embodiment, the strut-type structures can be made of the same material as the stent-like structure 1402, or other materials can be used. Further, instead of securing sensor 1404 in front of, or in back of anchoring device 1402, connection structures can be used to secure sensor 1404 within anchoring device 1402, but still near the middle of the vessel. In addition, as discussed above, sensor 1404 can be configured to communicate with implantable medical devices (IMDs), such as cardiac rhythm management device, and/or devices outside of a patient body.

Figure 19:
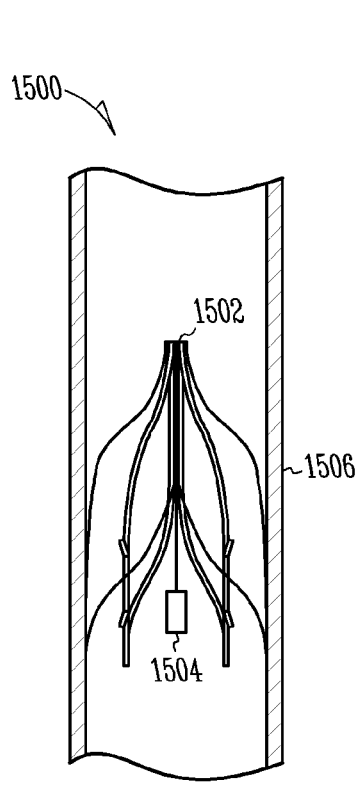
FIGS. 19-21 are cross-section views of yet other embodiments of sensor anchoring devices positioned within bodily cavities.
Figure 20:
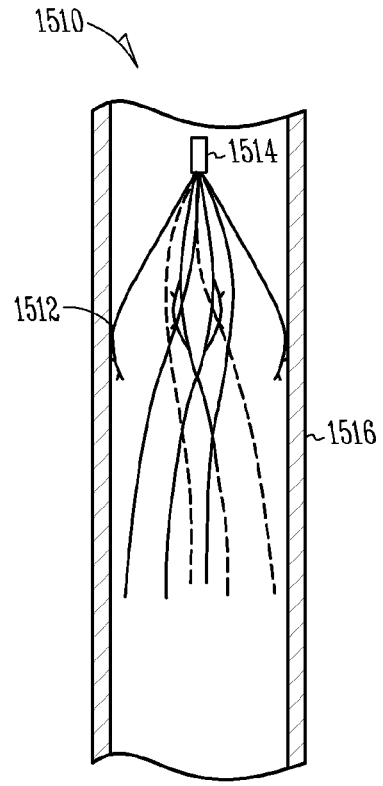
Figure 21:
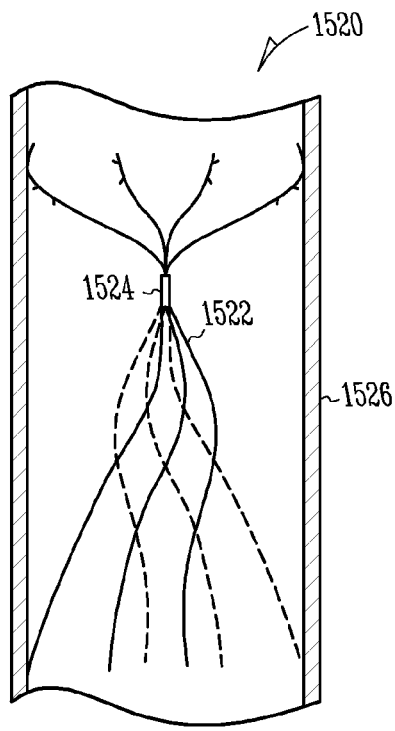

FIGS. 19-21 show additional embodiments of anchoring systems 1500, 1510, and 1520. In these embodiments, anchoring structures 1502, 1512, and 1522 can be used to secure sensors 1504, 1514, and 1524 within a bodily vessel (such as a blood vessel) 1506, 1516, and 1526, respectively. In some embodiments, the anchoring structure can be secured in place by surgical placement, and in other embodiments, the anchoring structure can be placed in a blood vessel, and then allowed to float or flow with the blood stream until the anchoring structure lodges in a suitable location to place the sensor.

In some embodiments (e.g., the embodiments illustrated in FIGS. 19-21), the anchoring structure can comprise a vena cava ("IVC") filter device having a sensor attached to it. For example, as illustrated in FIG. 19, a sensor 1504 can be connected to the IVC filter using a rigid or non-rigid tether connection. In other embodiments, such as the embodiments illustrated in FIGS. 20 and 21, sensors 1514 and 1524 can be incorporated into the structure of the IVC filter. In some embodiments, the sensor can be placed so that it is approximately near the center of the vessel to take advantage of the center flow of the vessel, and in other embodiments, the sensor can be configured so that it is secured near the wall of the vessel. Further, any suitable IVC filter device can be used. Examples of suitable IVC filters include, but are not limited to, an LGM filter, a Gunther tulipe filter, an Antheor filter, a DIL filter, a Keeper filter a FCP2002 filter, a Mobin-Uddin filter, a Kimray-Greenfield filter, a Simon nitinol filter, a titanium Greenfield filter, a Bird's Nest filter, or any other suitable IVC filter device. Further, in other embodiments, the anchoring structures may not be IVC filters, but may comprise structures having legs or extensions for securing a sensor within a vessel. In these embodiments, the legs or extensions can be configured to lodge in the vessel in a manner similar to the IVC filters, thus securing the sensor in place.

In one embodiment, the anchoring structures are designed to be secured in the pulmonary artery, which branches and tapers as it flows toward the lungs. In this particular embodiment, the anchoring structure can be placed in the pulmonary artery, and then allowed to flow with blood stream until the anchoring structure lodges in a desired location. Once secured, the sensor can collect the desired data measurements. As one skilled in the art will appreciate, the size of the anchoring structure can control the location in which it will lodge. Also, as one skilled in the art will appreciate, the anchoring structure can be placed in other blood vessels, as well. Thus, embodiments of the present invention are not limited to use in the pulmonary artery.

A discussed above, sensors 1504, 1514 and 1524 can be configured to communicate with implantable medical devices (IMDs), such as cardiac rhythm management devices, and/or devices outside of a patient's body.

Figure 22:
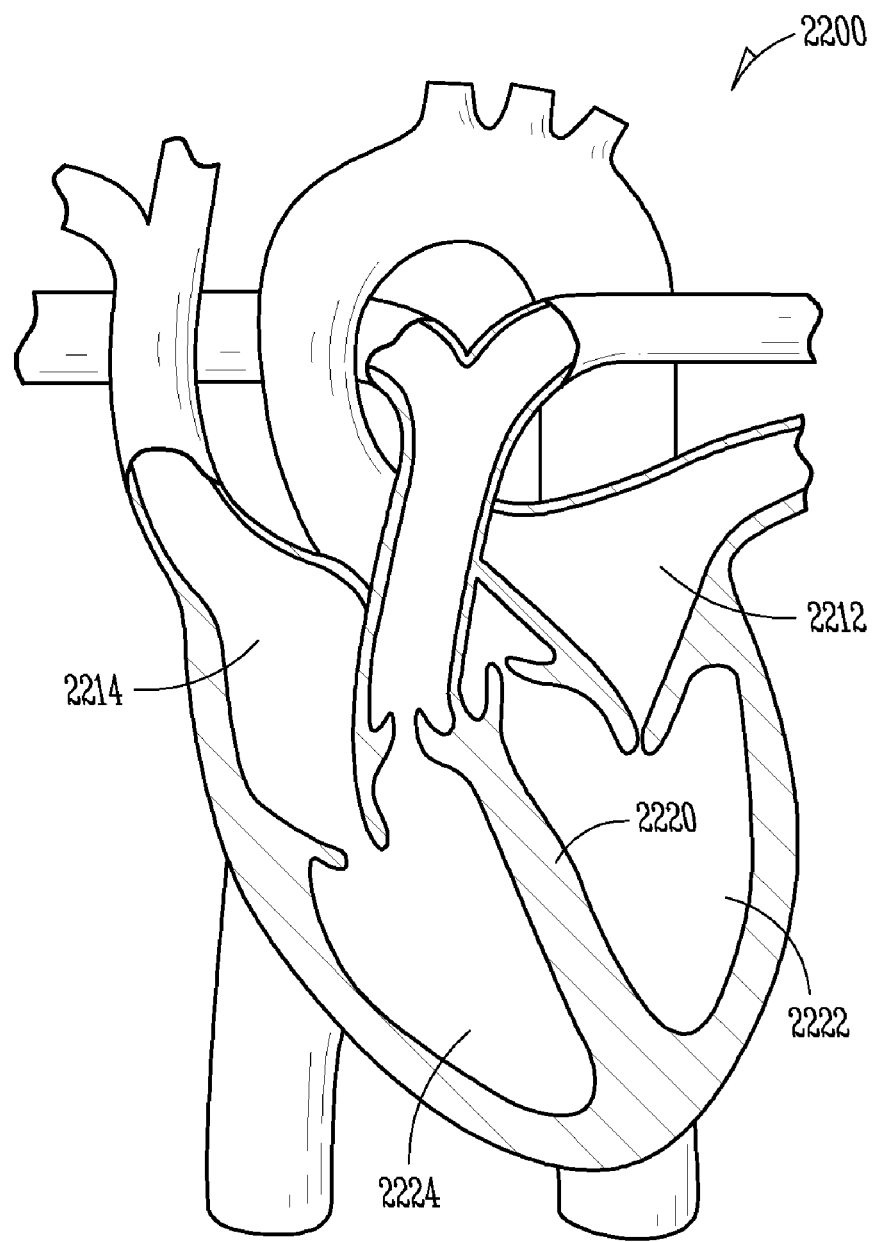
FIG. 22 is a cross-sectional view of a heart showing the septal walls.

FIG. 22 shows a cross-sectional view of a heart 2200. As illustrated, heart 2200 includes an atrium septal wall (not shown) separating left atrium 2212 from right atrium 2214, and a ventricular septal wall 2220 separating left ventricle 2222 from right ventricle 2224.

In accordance with another embodiment of the invention, a sensor anchoring device can be embedded in a separating or enclosing wall of the heart, for example, atrium septal wall or ventricular septal wall 2220. In FIGS. 23A-23E, one method of inserting a sensor anchoring device in accordance with this embodiment is shown. In this particular embodiment, a sensor 2308 can be embedded inside or attached to a plug-like anchoring structure, which then can be placed in any cardiac separating or enclosing wall 2304 (e.g., the septal wall). In accordance with this particular embodiment, a physician may be able to perform two functions at once: (1) fill a preexisting hole or slit in a cardiac separating wall in order to prevent blood from crossing from one side to another; and (2) use the plug as an enclosure for the placement of a physiologic parameter sensor. In other embodiments, a physician may create a hole or slit to place a sensor, and the plug-like anchoring structure can be used to place the sensor and plug and/or seal the slit or hole.

Figure 23A:
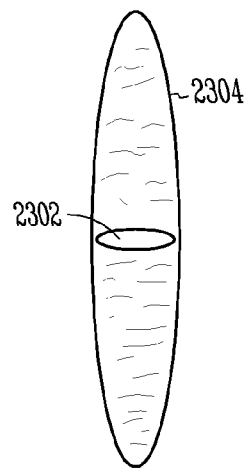
FIGS. 23A-23E are diagrams illustrating one embodiment of a method for anchoring a sensor within the septal wall of the heart.
Figure 23B:
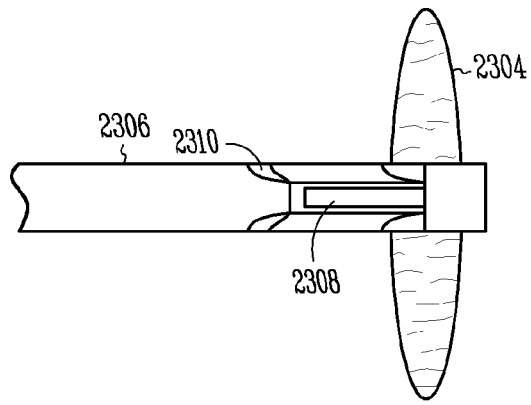
Figure 23C:
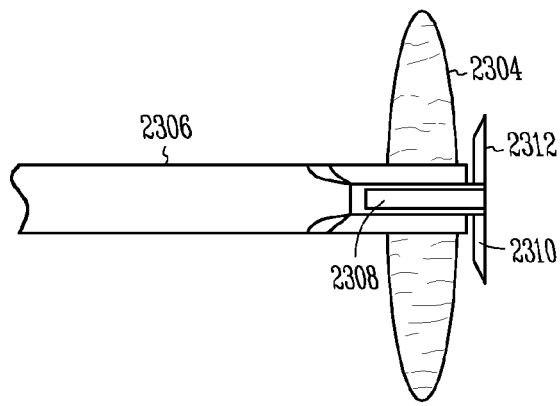
Figure 23D:
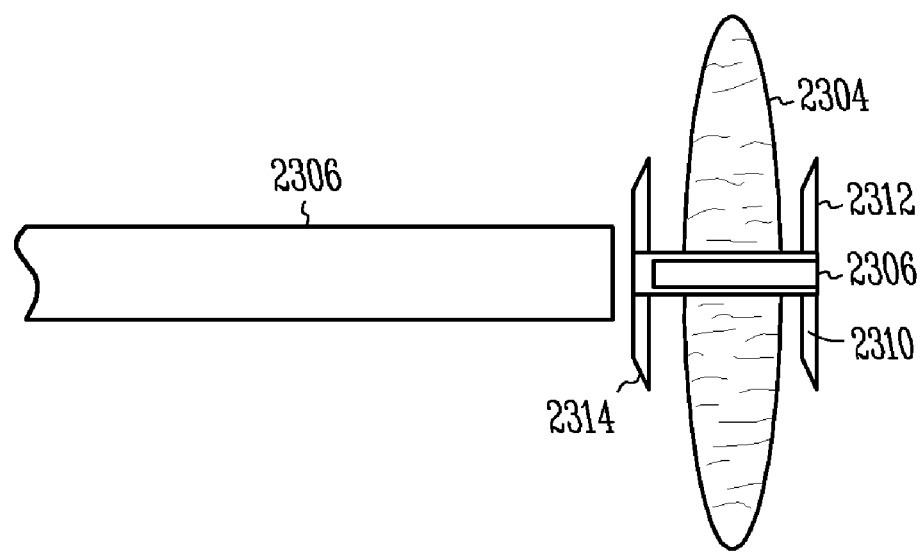
Figure 23E:
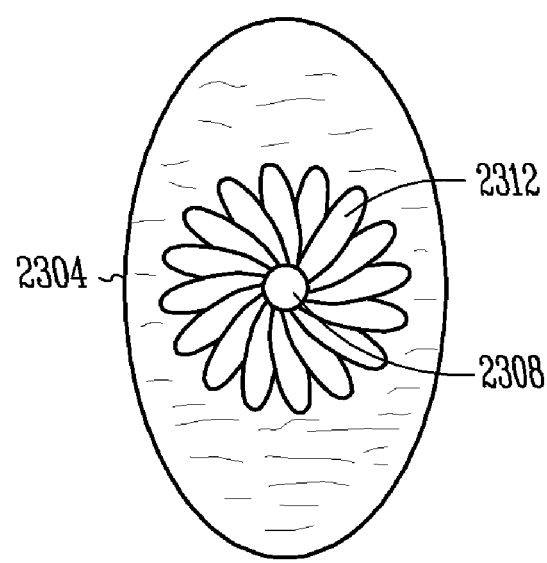

FIGS. 23A-23E illustrate one embodiment of a method for anchoring a sensor in a cardiac separating wall, such as the septal wall. FIG. 23A illustrates a cardiac separating wall (e.g., septal wall) 2304 with a hole or slit 2302 for placing an anchoring structure with sensor. As illustrated in FIG. 23B a physiologic parameter sensor 2308 embedded in or attached to a plug-like anchoring structure 2310 can be inserted into a pre-anchoring slit 2302 (either a nature hole or a surgically created hole or slit) using, for example, a guide catheter 2306. In this embodiment, the guide catheter has the anchor/sensor assembly embedded in it. To place the plug-like anchor 2310 (with sensor 2308) in the desired location, the guide catheter 2306 is placed in the hole or slit 2302 (FIG. 23B). Then, the guide catheter 2306 is retracted, causing plug ends 2312 and 2314 of the anchor device 2310 to expand (FIGS. 23C and 23D). The plug ends 2312 and 2314 form a seal so that blood cannot flow through hole 2302 or around anchor structure 2310. FIG. 23E shows an end view of plug end 2312 of the anchoring device 2310. In one embodiment, the anchoring device can be a septal plug currently known in the art. In this embodiment, however, the septal plug is equipped with a sensor, as discussed.

Figure 24:
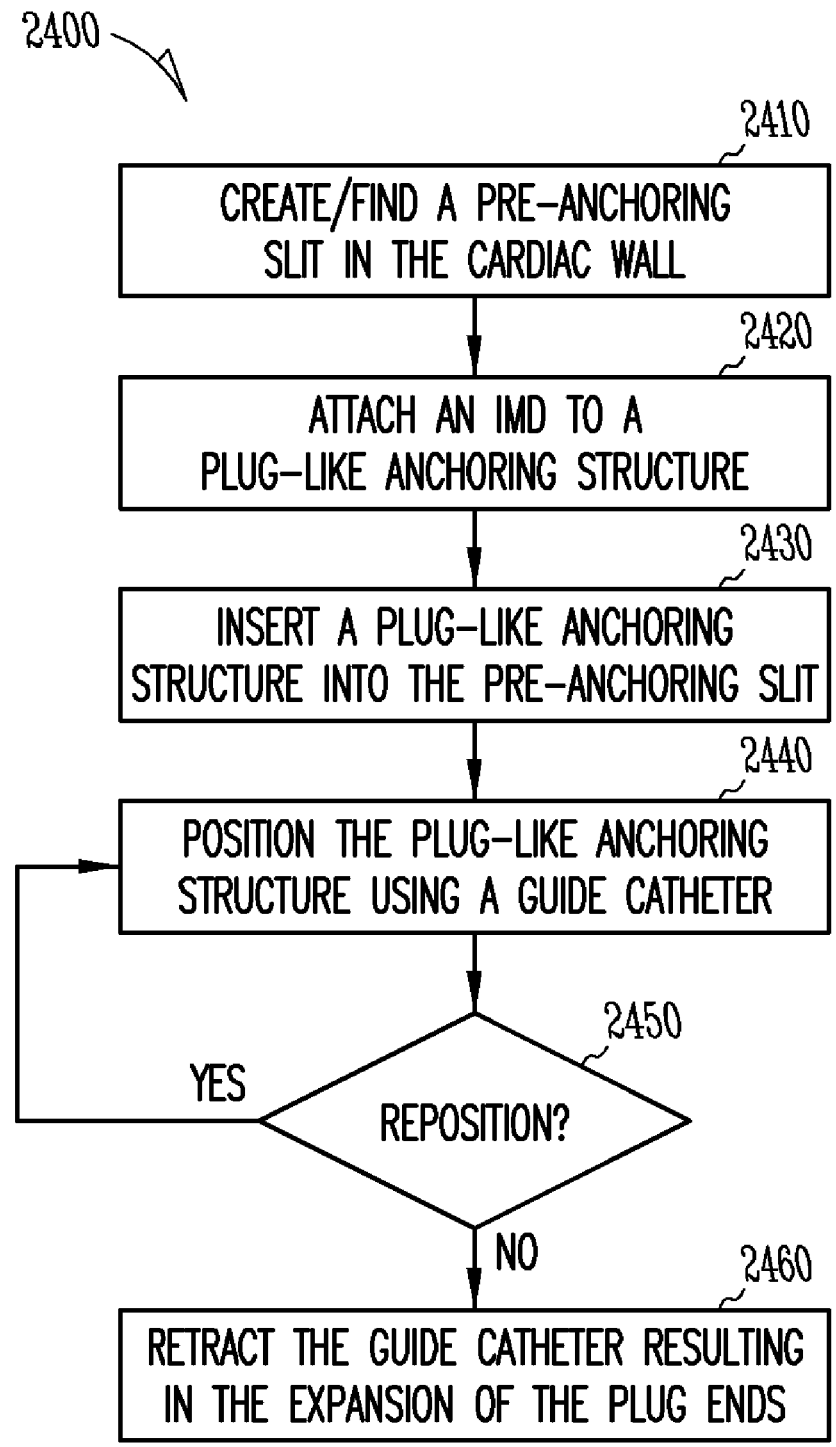
FIG. 24 is a flow diagram illustrating delivering, positioning, and anchoring a plug-like structure into a pre-anchoring slit according to one embodiment of the present invention.

FIG. 24 is a flow diagram 2400 illustrating delivering, positioning, and anchoring a plug-like structure into a pre-anchoring slit according to one embodiment of the present invention. At block 2410, a pre-anchoring slit is located, or surgically created if one does not exist, in the cardiac wall. An IMD is attached to a plug-like anchoring structure at step 2420. Then, the plug-like anchoring structure is inserted into the pre-anchoring slit at step 2430. At step 2440, using a guide catheter, the plug-like anchoring structure is positioned and then repositioned, at step 2450, as necessary. Once the final placement of the plug-like anchoring structure has been achieved, the guide catheter is retracted, resulting in the expansion of the plug ends at step 2460.

Figure 25:
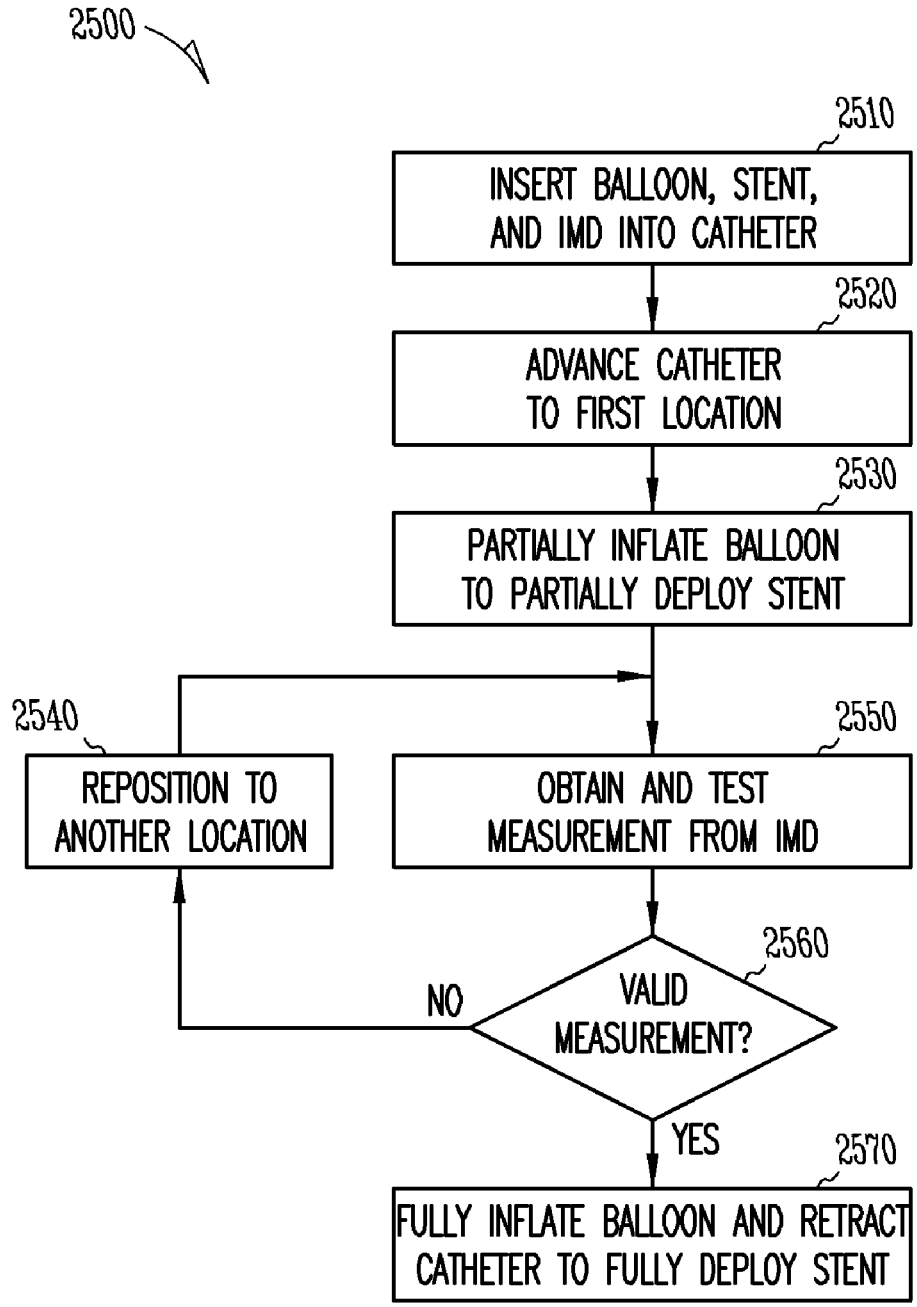
FIG. 25 is a flow diagram illustrating an exemplary algorithm for controllably positioning and anchoring an implantable medical device at a desired location.

FIG. 25 is a flow diagram illustrating an exemplary algorithm 2500 for controllably positioning and anchoring an IMD at a location in a bodily vessel. At block 2510, a deflated balloon is inserted through a collapsed stent and an IMD is attached to the stent using, for example, one of the attachment methods described above. The stent with balloon and IMD are then inserted into a catheter.

At block 2520, the catheter is advanced into the bodily vessel to a first location. The first location is typically selected to be close to the desired location. At block 2530, the balloon is partially inflated, thereby partially expanding the stent. By partially inflating the balloon, the positioning can be controlled by enabling later repositioning, if desired. With the balloon partially inflated, one or more physiologic parameter measurements are obtained from the IMD (e.g., blood pressure, temperature, strain, motion, etc.) at block 2550. The measurements are tested for validity. Testing the measurements can involve determining whether numerical values are detected and that the values are reasonable.

At decision block 2560, it is determined whether the measurements are valid. If the measurements are not valid, block 2540 repositions the stent to another location by moving the catheter. After the stent is repositioned to the other location, block 2550 again obtains and tests measurements from the IMD. Repositioning can continue until block 2560 determines that the measurements are valid. If the measurements are valid, the balloon is fully inflated at block 2570 at the current location. By fully inflating the balloon, the stent if fully expanded. The fully expanded stent frictionally engages with walls of the bodily vessel to secure the stent within the bodily vessel.

As discussed, FIG. 25 illustrates a process for positioning a sensor using a balloon-deployable stent. A different embodiment could include self-expanding stent that carries the sensor. In this embodiment, the self-expanding stent can be partially deployed and tested prior to full deployment. If test measurements taken after partial deployment are not informative, invalid, or for any other reason, considered undesirable, or for any other reason (e.g., patient discomfort), the self-expanding stent can be moved to another location, tested, and so on. When valid test measurements are obtained at a location, the stent can be fully expanded at that location.

It is to be understood that the above description is intended to be illustrative, and not restrictive. For example, the above-described embodiments (and/or aspects thereof) may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "comprising" are open-ended, that is, a system, device, article, or process that includes elements in addition to those listed after such a term in a claim are still deemed to fall within the scope of the claim.

What is claimed is:

1. A system for use in a body having a pulmonary artery, comprising:
   an implantable pulmonary artery pressure (PAP) sensor configured to be mounted on an interior wall of the pulmonary artery and sense a PAP signal indicative of a volume of circulating blood; and
   an implantable medical device communicatively coupled to the implantable PAP sensor via a wireless telemetry link, the implantable medical device comprising:
      a signal processor adapted to process the PAP signal; and
      a hypovolemia detector adapted to produce a diastolic PAP (DPAP) using the processed PAP signal, detect hypovolemia using at least the DPAP, and produce a hypovolemia detection signal indicative of the detection of hypovolemia.

2. The system of claim 1, comprising a stent-like anchoring structure coupled to the implantable PAP sensor and configured to anchor the implantable PAP sensor to the pulmonary artery.

3. The system of claim 2, wherein the stent-like structure comprises a mesh structure, and the implantable PAP sensor is embedded in the mesh structure.

4. The system of claim 3, wherein the implantable medical device is communicatively coupled to the implantable PAP sensor via an ultrasonic telemetry link.

5. The system of claim 1, wherein the signal processor comprises an atmospheric pressure adjustment module adapted to adjust the PAP signal using an atmospheric pressure, and further comprising an external pressure sensor communicatively coupled to the implantable medical device, the external pressure sensor comprising a barometer to sense the atmospheric pressure.

6. The system of claim 1, wherein the signal processor comprises a posture adjustment module adapted to adjust the PAP signal using a posture signal, and further comprising a posture sensor adapted to sense the posture signal.

7. The system of claim 1, wherein the PAP signal processor comprises a respiration adjustment module adapted to adjust the PAP signal using a respiratory signal, and further comprising a respiratory sensor adapted to sense the respiratory signal.

8. The system of claim 1, wherein the hypovolemia detector comprises:
   a PAP attribute producer adapted to produce a PAP attribute using the processed PAP signal; and
   a detection comparator adapted to detect hypovolemia by comparing the PAP attribute to a hypovolemia-detection threshold and to produce the hypovolemia detection signal when the hypovolemia is detected.

9. The system of claim 8, wherein the PAP attribute producer is adapted to produce the DPAP and one or more of a systolic PAP (SPAP), a PAP pulse pressure, a timing of a dicrotic notch in the PAP signal relative to another PAP feature such as a peak (SPAP), a maximum rate of change in PAP (maximum dPAP/dt), and a minimum rate of change in PAP (minimum dPAP/dt), a (SPAP) time interval, and a DPAP time interval.

10. The system of claim 8, wherein the PAP attribute is a mean PAP (MPAP), and the PAP attribute producer comprises:
   a DPAP producer adapted to produce the DPAP using the processed PAP signal;
   a systolic PAP (SPAP) producer adapted to produce an SPAP using the processed PAP signal; and
   an MPAP calculator adapted to calculate the MPAP using the DPAP and the SPAP.

11. The system of claim 8, wherein the hypovolemia detector further comprises a baseline generator adapted to produce a baseline of the PAP attribute, and wherein the detection comparator is adapted to produce the hypovolemia detection signal by comparing the PAP attribute to a predetermined percentage of the baseline of the PAP attribute.

12. The system of claim 11, wherein the baseline generator comprises:
   a short-term PAP attribute producer adapted to produce short-term value of the PAP attribute on a periodic basis, the short-term PAP attribute producer including:
      a PAP sampler adapted to produce samples of the PAP signal; and
      a short-term PAP attribute calculator adapted to calculate each of the short-term values of the PAP attribute by averaging a plurality of the samples of the PAP signal; and
   a moving averager adapted to produce the baseline of the PAP attribute by calculating a moving average of a plurality of the short-term values of the PAP attribute on the periodic basis.

13. The system of claim 8, wherein the hypovolemia detector further comprises a prediction comparator adapted to produce a hypovolemia prediction signal indicative of a prediction of hypovolemia by comparing the PAP attribute to a hypovolemia-prediction threshold.

14. The system of claim 1, wherein the implantable medical device further comprises a hypovolemia detection enhancement module to enhance the detection of hypovolemia using one or more enhancement signals including one or more of a signal indicative of loss of body weight, a signal indicative of increased heart rate, a signal indicative of increased respiratory rate, a signal indicative of postural hypotension, a signal indicative of decreased pulse pressure, a signal indicative of delayed dicrotic notch, a signal indicative of increased hemoglobin, and a signal indicative of increased hematocrit.

15. The system of claim 14, further comprising a warning message generator adapted to produce a warning message based on at least one of the hypovolemia detection signal and the one or more enhancement signals, the warning message including at least one of an alarm signal indicative of an occurrence of the hypovolemia and a caution signal indicative of an elevated risk of hypovolemia.

16. The system of claim 1, wherein the implantable medical device further comprises:
   a therapy delivery device adapted to deliver one or more therapies; and
   a therapy controller adapted to control the delivery of the one or more therapies using at least the hypovolemia detection signal.

17. The system of claim 1, wherein the implantable medical device further comprises an edema detector adapted to produce an edema detection signal indicative of a detection of edema.

18. The system of claim 17, wherein the implantable medical device further comprises:
   a therapy delivery device adapted to deliver one or more therapies; and a therapy controller adapted to control the delivery of the one or more therapies using at least the hypovolemia detection signal and the edema detection signal.

19. The system of claim 18, wherein the therapy delivery device comprises a drug delivery device adapted to deliver one or more diuretic agents.

20. A method for operating an implantable medical device, the method comprising:
receiving a pulmonary artery pressure (PAP) signal from an implantable PAP sensor via a wireless telemetry link, the implantable PAP sensor mounted on an interior wall of a pulmonary artery to sense the PAP signal;
producing a diastolic PAP (DPAP) using the PAP signal; and
detecting hypovolemia using at least the DPAP using the implantable medical device.

21. The method of claim 20, wherein receiving the PAP signal comprises receiving the PAP signal from the implantable PAP sensor anchored to the pulmonary artery using a stent-like anchoring structure.

22. The method of claim 20, wherein detecting the hypovolemia comprises:
producing a PAP attribute using the PAP signal;
detecting a hypovolemia by comparing the PAP attribute to a hypovolemia-detection threshold; and
producing a hypovolemia detection signal when the hypovolemia is detected.

23. The method of claim 22, further comprising:
sensing an atmospheric pressure; and
adjusting the PAP signal using the atmospheric pressure prior to producing the PAP attribute.

24. The method of claim 22, further comprising:
sensing a posture signal; and
adjusting the PAP signal using the posture signal prior to producing the PAP attribute.

25. The method of claim 22, further comprising:
sensing a respiratory signal indicative of respiratory cycles; and
adjusting the PAP signal for effects related to respiratory cycles.

26. The method of claim 22, wherein the PAP attribute is a mean PAP (MPAP), and producing the PAP attribute comprises:
detecting a systolic PAP (SPAP) from the PAP signal; and
calculating the MPAP using the DPAP and the SPAP.

27. The method of claim 26, wherein calculating the MPAP comprises using an equation:

MPAP=(2·DPAP+SPAP)/3.

28. The method of claim 27, wherein the hypovolemia-detection threshold is in a range of approximately 5 to 10 mmHg.

29. The method of claim 22, further comprising producing a baseline of the PAP attribute, and wherein the hypovolemia-detection threshold is a percentage of the baseline of the PAP attribute, the percentage being in a range of approximate 60% to 80%.

30. The method of claim 29, further comprising:
producing a plurality of samples of the PAP signal on a periodic basis using a predetermined period;
calculating a short-term value of the PAP attribute by averaging the samples of the plurality of samples of the PAP signal; and
producing the baseline of the PAP attribute by calculating a moving average of a plurality of the short-term values of the PAP attribute on the periodic basis.

31. The method of claim 30, wherein the predetermined period is in a range of approximately 2 to 12 hours, the plurality of samples of the PAP signal includes approximately 5 to 30 samples, and the plurality of short-term MPAPs are produced over a duration of approximately 5 to 45 days.

32. The method of claim 22, comprising:
comparing the PAP attribute to a hypovolemia-prediction threshold; and
producing a hypovolemia prediction signal indicative of a prediction of hypovolemia based on an outcome of the comparison.

33. The method of claim 22, further comprising enhancing the detection of the hypovolemia using one or more enhancement signals including one or more of a signal indicative of loss of body weight, a signal indicative of increased heart rate, a signal indicative of increased respiratory rate, a signal indicative of postural hypotension, a signal indicative of decreased pulse pressure, a signal indicative of delayed dicrotic notch, a signal indicative of increased hemoglobin, and a signal indicative of increased hematocrit.

34. The method of claim 33, comprising producing at least one of an alarm signal and a caution signal based on at least one of the hypovolemia detection signal and the one or more enhancement signals, the alarming signal indicative of an occurrence of the hypovolemia, the caution signal indicative of an elevated risk of hypovolemia.

35. The method of claim 22, further comprising:
receiving a further physiological signal indicative of a fluid retention;
detecting an edema from the further physiological signal using the implantable medical device; and
producing an edema detection signal when the edema is detected.

36. The method of claim 35, further comprising:
delivering one or more therapies; and
controlling the delivery of the one or more therapies using the hypovolemia detection signal and the edema detection signal.

37. The method of claim 36, wherein delivering the one or more therapies comprises delivering one or more diuretic agents.

* * * * *